US012414955B2

(12) United States Patent
Flynn

(10) Patent No.: US 12,414,955 B2
(45) Date of Patent: Sep. 16, 2025

(54) ANTI-VIRAL ACTIVITY OF VPS34 INHIBITORS

(71) Applicant: Deciphera Pharmaceuticals, LLC, Waltham, MA (US)

(72) Inventor: Daniel L. Flynn, Waltham, MA (US)

(73) Assignee: Deciphera Pharmaceuticals, LLC, Waltham, MA (US)

(*) Notice: Subject to any disclaimer, the term of this patent is extended or adjusted under 35 U.S.C. 154(b) by 0 days.

(21) Appl. No.: 17/534,795

(22) Filed: Nov. 24, 2021

(65) Prior Publication Data

US 2022/0193083 A1 Jun. 23, 2022

Related U.S. Application Data

(60) Provisional application No. 63/118,507, filed on Nov. 25, 2020.

(51) Int. Cl.
*A61K 31/5377* (2006.01)
*A61K 31/5386* (2006.01)
*A61P 31/14* (2006.01)

(52) U.S. Cl.
CPC ...... *A61K 31/5377* (2013.01); *A61K 31/5386* (2013.01); *A61P 31/14* (2018.01)

(58) Field of Classification Search
CPC .. A61K 31/5377; A61K 31/5386; A61P 31/14
See application file for complete search history.

(56) References Cited

U.S. PATENT DOCUMENTS

| | | | |
|---|---|---|---|
| 8,846,670 B2 | 9/2014 | Bacque et al. | |
| 10,787,501 B1 | 9/2020 | Babb et al. | |
| 11,179,399 B2 | 11/2021 | Martinsson et al. | |
| 11,633,403 B2 | 4/2023 | Martinsson et al. | |
| 2014/0275003 A1 | 9/2014 | Barsanti et al. | |

FOREIGN PATENT DOCUMENTS

| | | | |
|---|---|---|---|
| WO | WO-2004/048365 A1 | 6/2004 | |
| WO | WO-2004/112720 A2 | 12/2004 | |
| WO | WO-2009/014633 A1 | 1/2009 | |
| WO | WO-2010/052569 A2 | 5/2010 | |
| WO | WO-2011/001113 A2 | 1/2011 | |
| WO | WO-2013/190510 A2 | 12/2013 | |
| WO | WO-2014/043442 A1 | 3/2014 | |
| WO | WO-2014/151616 A1 | 9/2014 | |
| WO | WO-2015/030057 A1 | 3/2015 | |
| WO | WO-2016/044662 A1 | 3/2016 | |
| WO | WO-2017/140841 A1 | 8/2017 | |
| WO | WO-2017140843 A1 * | 8/2017 | ......... A61K 31/4745 |
| WO | WO-2019/038384 A1 | 2/2019 | |
| WO | WO-2019/038387 A1 | 2/2019 | |
| WO | WO-2019/038389 A1 | 2/2019 | |
| WO | WO-2019/038390 A1 | 2/2019 | |
| WO | WO-2022/015823 A2 | 1/2022 | |
| WO | WO-2022/115543 A1 | 6/2022 | |
| WO | WO-2022/115545 A1 | 6/2022 | |
| WO | WO-2022/115546 A1 | 6/2022 | |
| WO | WO-2022/115549 A1 | 6/2022 | |
| WO | WO-2022/115558 A1 | 6/2022 | |
| WO | WO-2022/115562 A1 | 6/2022 | |

OTHER PUBLICATIONS

Silva et al. "Inhibitory of VPS34 and lipid metabolism suppress SARS-CoV-2 replication," Biorxiv.org https://www.biorxiv.org/content/10.1101/2020.07.18.210211v1.full. Pdf (Year: 2020).*

Yuen et al. "Supression of SARS-CoV-2 infection in ex-vivo human lung tissue by targeting class III phosphoinositide 3-kinase," J. Med. Virol. 2021; 93 2076-2083, First published: Oct. 7, 2020 https://doi.org/10.1002/jmv.26583 (Year: 2020).*

Kumar et al. "Repurposing antiviral protease inhibitors using extracellular vesicles for potential therapy of COVID-19," MDPI, Apr. 2020, https://www.mdpi.com/1999-4915/12/5/486 (Year: 2020).*

Aggarwal, V. et al., "Reaction of a Keto-ketene S, N-Acetals with Cyanoacetamide: A new general Method for Substituted and Fused 4-(N-Alkylamino-, N-Arylamino- or N-Morpholino )-3-cyano-2(1H)-pyridones", SYNTHESIS, 1982, 1982(03): 214-216, George Thieme Verlag—Stuttgart—New York.

Anonymous, "Lilly announces proof of concept data for neutralizing antibody LY-CoV555 in the COVID-19 outpatient setting", (Sep. 16, 2020), XP055894838, 2 pages.

Bago, R. et al., "Characterization of VPS34-IN1, a selective inhibitor of Vps34, reveals that the phosphatidylinositol 3-phosphate-binding SGK3 protein kinase is a downstream target of class III phosphoinositide 3-kinase," Biochem. J., (2014), 463, pp. 413-427.

Coffman, K. et al., "6-Amino-4-(pyrimidin-4-yl)pyridones: Novel glycogen synthase kinase-3? inhibitors," Bioorganic & Medicinal Chemistry Letters, (2011), vol. 21, pp. 1429-1433, 5 pages.

Dowdle, W. E. et al., "Selective VPS34 inhibitor blocks autophagy and uncovers a role for NCOA4 in ferritin degradation and iron homeostasis in vivo," Nature Cell Biology, (Nov. 2014), v. 16, No. 11, 23 pages.

Drozdzal, S. et al., "FDA approved drugs with pharmacotherapeutic potential for SARS-CoV-2 (COVID-19) therapy", Drug Resist. Updates, (Jul. 15, 2020), vol. 53, XP086397821.

Honda, A. et al., "Potent, Selective, and Orally Bioavailable Inhibitors of VPS34 Provide Chemical Tools to Modulate Autophagy in Vivo," ACS Med. Chem. Lett. (2016), v. 7, pp. 72-76.

International Search Report and Written Opinion of PCT/US2021/060762 dated Mar. 15, 2022, 20 pages.

Pasquier, B., "SAR405, a PIK3C3/Vps34 inhibitor that prevents autophagy and synergizes with MTOR inhibition in tumor cells," Autophagy, (Apr. 2015), v. 11, No. 4, pp. 725-726.

Poduri, R. et al., "Drugs targeting various stages of the SARS-CoV-2 life cycle: Exploring promising drugs for the treatment of Covid-19", Cell Signalling, (Oct. 2020), vol. 74, p. 109721, XP055845504.

Roedig, A. et al., "Nucleophile Substitutionen em (Z)-Percholor-1,3-butadien-1-carbonitril mit Natriumphemolat und sekundären aliphatischen Aminen", Chemische Berichte, 1982, 115(5): 1733-1738, XP055269826, DE.

(Continued)

*Primary Examiner* — Yong S. Chong
(74) *Attorney, Agent, or Firm* — Goodwin Procter LLP

(57) ABSTRACT

Described herein, in part, are methods of treating viral infections, such as coronavirus infections, in patients in need thereof, comprising administering to the patients a VPS34 inhibitor.

1 Claim, 7 Drawing Sheets

(56) References Cited

OTHER PUBLICATIONS

Ronan, B. et al., “A highly potent and selective Vps34 inhibitor alters vesicle trafficking and autophagy,” Nature Chemical Biology, (Dec. 2014), v. 10, pp. 1013-1020.
Shi, C. et al., “Comprehensive Landscape of Heparin Therapy for COVID-19”, Carbohydr. Polym., (Oct. 22, 2020), vol. 254, XP086423466.
Silvas, J. A. et al., “Inhibitors of VPS34 and fatty-acid metabolism suppress SARS-CoV-2 replication,” Cell reports 36, (2021), 20 pages.
Wang, M. et al., “Remdesivir and chloroquine effectively inhibit the recently emerged novel coronavirus (2019-nCoV) in vitro”, Cell Research, (2020), 3 pages.
Williams, C. G. et al., “Inhibitors of VPS34 and fatty-acid metabolism suppress SARS-CoV-2 replication”, Cell Rep., Aug. 3, 2021), vol. 36(5), p. 109479, XP055894511.
International Search Report and Written Opinion of PCT/US2021/060740 dated Apr. 28, 2022, 9 pages.
International Search Report and Written Opinion of PCT/US2021/060742 dated May 3, 2022, 18 pages.
International Search Report and Written Opinion of PCT/US2021/060743 dated Apr. 26, 2022, 10 pages.
International Search Report and Written Opinion of PCT/US2021/060747 dated May 3, 2022, 10 pages.
International Search Report and Written Opinion of PCT/US2021/060758 dated Mar. 14, 2022, 16 pages.
Zharko et al. “Identification of Required Host Factors for SARS-CoV-2 Infection in Human Cells”, Cell, Elsevier, Amsterdam NL, 2020, 184(1), pp. 92-105.
SynergyFinder—User Documentation, 2022 (https://synergyfinder.fimm.fi/synergy/synfin_docs/), 24 pages.
Zheng et al. “User tutorial of the SynergyFinder Plus” (https://bioconductor.org/packages/release/bioc/vignettes/synergyfinder/inst/doc/User_tutorual_of the_SynergyFinder_plus.html#heatmap), access Feb. 1, 2024, 42 pages.

* cited by examiner

SARS-COV-1

IC50 0.65 uM

CC50 > 30 uM

ANTI-VIRAL ACTIVITY OF VPS34 INHIBITORS

CROSS-REFERENCE

This application claims priority to U.S. Provisional Application No. 63/118,507 filed Nov. 25, 2020, which is incorporated herein by reference in its entirety.

BACKGROUND

There is an unmet medical need to identify agents for the therapeutic treatment of SARS CoV-2 and related coronaviruses. It has been reported that +RNA viruses, including coronaviruses, require the formation of double membrane vesicles during the viral replication process. These double membrane vesicles resemble autophagosomes. That the formation of these vesicles is important for viral replication is further supported by the finding that +RNA viruses, including coronaviruses, encode a nonstructural protein, NSP6, dedicated to the initiation of the formation of these double membrane vesicles upon infection of host cells. These vesicles are required during viral replication to protect the double helix viral RNA from host cell RNAases that would otherwise degrade the viral RNA and thwart viral replication. siRNA interference of LC-3, a protein essential for autophagosome formation, has been demonstrated to block coronavirus replication. Furthermore, dual-labeling studies have demonstrated co-localization of the viral replicase protein nsp8, nsp2, and nsp3 with LC-3. Thus, evidence points toward the requirement of these double membrane vesicles for viral replication of coronaviruses, including SARS CoV-2.

A novel therapeutic approach for patients with COVID-19 or other coronavirus infections is targeting and blocking the formation of these double membrane vesicles required for viral replication. Genetic studies have shown that some +RNA viruses require ULK kinase to initiate the formation of infected cell autophagosomes, while other +RNA viruses require VPS34 kinase to initiate the formation of infected cell autophagosomes. Recently it has been disclosed that VPS34 kinase is required for formation of double membrane vesicles in SARS CoV-2 and related viruses. The packaging of coronavirus progeny in an infected cell with double membrane vesicles may also allow for spread of viruses from an infected cell to cause the infection of other cells. During this process, protection of coronaviruses, including SARS CoV-2, within double membrane vesicles may shield viral spread from the immune system. Hence VPS34 inhibitors provide the potential for inhibiting viral replication of coronaviruses, including SARS CoV-2.

In addition to playing a role in the formation of double membrane autophagosomes, VPS34 kinase also plays an obligate role in a related endosomal pathway that forms double membrane vesicles. The endosomal pathway may also play a role in viral entry into host cells infected with coronaviruses, including SAR COV-2. Endosomes have also been demonstrated to play a role in viral trafficking post viral entry. Thus, inhibitors of VPS34 kinase may potentially inhibit several steps during the coronavirus replication cycle: 1) inhibition of viral entry; 2) inhibition of viral trafficking post-entry; and 3) inhibition of the viral replicase complex.

SUMMARY

Provided herein, in part, are methods of treating viral infections, methods of inhibiting transmission of a virus, methods of inhibiting viral replication, methods of minimizing expression of viral proteins, or methods of inhibiting virus release using VPS34 inhibitors.

For example, in one embodiment, described herein is a method of ameliorating or treating a viral infection in a patient in need thereof, comprising administering to the patient a therapeutically effective amount of a compound represented by Formula I:

Formula I

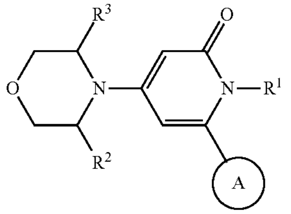

or a pharmaceutically acceptable salt, stereoisomer, or tautomer thereof, wherein: $R^1$, $R^2$, and $R^3$ are independently selected from the group consisting of H, $C_1$-$C_3$haloalkyl, and $C_1$-$C_3$alkyl; A represents:

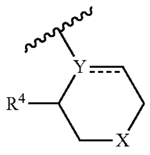 , 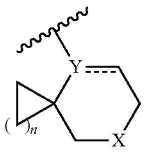 , or 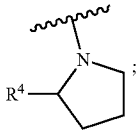 ;

$\overline{---}$ is a single bond or a double bond; X is selected from the group consisting of $CH_2$, S, SO, $SO_2$, $NR^5$, $NCOR^5$, $NCOR^9$, $NCOCH_2R^9$, O, and a bond; Y is selected from the group consisting of N, CH, and C, provided that, when Y is CH, $\overline{---}$ is a single bond; n is selected from 1, 2, 3 and 4; each $R^4$ is independently selected from the group consisting of H, halogen, $COR^6$, $C_1$-$C_6$alkyl, $C_1$-$C_3$alkoxy$C_1$-$C_3$alkyl, $C_1$-$C_6$alkoxy, $C_3$-$C_6$cycloalkyl, $C_3$-$C_6$heterocyclyl, $C_1$-$C_3$cyanoalkyl, $C_1$-$C_3$haloalkyl, aryl, and heteroaryl, wherein said aryl and said heteroaryl are optionally substituted with one or more $R^7$; $R^5$ is selected from the group consisting of H, $C_1$-$C_3$fluoroalkyl, $C_1$-$C_3$alkyl, $C_1$-$C_3$alkoxy$C_1$-$C_3$alkyl, and $C_3$-$C_6$cycloalkyl; $R^6$ is selected from the group consisting of $C_1$-$C_3$alkoxy, N—$C_1$-$C_3$alkylamino, N.N-di$C_1$-$C_3$alkylamino, 1-pyrrolidinyl, 1-piperidinyl, and 1-azetidinyl; each $R^7$ is independently selected from the group consisting of $C_1$-$C_6$alkyl, $C_3$-$C_6$cycloalkyl, $C_1$-$C_3$alkoxy$C_1$-$C_3$alkyl, $C_1$-$C_3$haloalkyl, halogen, N—$C_1$-$C_3$alkylamino, N.N-di$C_1$-$C_3$alkylamino, $C_1$-$C_3$haloalkoxy and $C_1$-$C_3$alkoxy; $R^9$ is selected from the group consisting of $C_1$-$C_3$alkyl, $C_1$-$C_3$alkoxy, $C_3$-$C_6$cycloalkyl, heterocyclyl, phenyl and a monocyclic heteroaryl, wherein said heterocyclyl, said phenyl and said monocyclic heteroaryl are optionally substituted with one or two $R^8$; and each $R^8$ is independently selected from the group consisting of halogen, $C_1$-$C_3$haloalkyl and $C_1$-$C_3$alkyl.

In one embodiment, described herein is a method of ameliorating or treating a viral infection in a patient in need thereof, comprising administering to the patient a therapeutically effective amount of a compound represented by Formula I:

Formula I

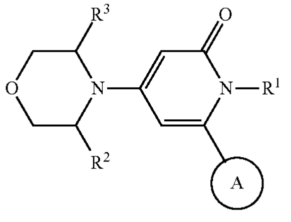

or a pharmaceutically acceptable salt, stereoisomer, or tautomer thereof, wherein: $R^1$, $R^2$, and $R^3$ are independently selected from the group consisting of H, $C_1$-$C_3$haloalkyl, and $C_1$-$C_3$alkyl; A represents:

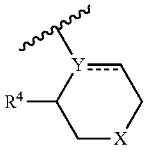

or

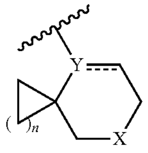

;

- - - is a single bond or a double bond; X is selected from the group consisting of $CH_2$, S, SO, $SO_2$, $NR^5$, $NCOR^5$, $NCOR^9$, $NCOCH_2R^9$, O, and a bond; Y is selected from the group consisting of N, CH, and C, provided that, when Y is CH, - - - is a single bond; n is selected from 1, 2, 3 and 4; $R^4$ is selected from the group consisting of H, halogen, $COR^6$, $C_1$-$C_6$alkyl, $C_1$-$C_3$alkoxy$C_1$-$C_3$alkyl, $C_1$-$C_6$alkoxy, $C_3$-$C_6$cycloalkyl, $C_3$-$C_6$heterocyclyl, $C_1$-$C_3$cyanoalkyl, $C_1$-$C_3$haloalkyl, aryl, and heteroaryl, wherein said aryl and said heteroaryl are optionally substituted with one or more $R^7$; $R^5$ is selected from the group consisting of H, $C_1$-$C_3$fluoroalkyl, $C_1$-$C_3$alkyl, $C_1$-$C_3$alkoxy$C_1$-$C_3$alkyl, and $C_3$-$C_6$cycloalkyl; $R^6$ is selected from the group consisting of $C_1$-$C_3$alkoxy, N—$C_1$-$C_3$alkylamino, N.N-di$C_1$-$C_3$alkylamino, 1-pyrrolidinyl, 1-piperidinyl, and 1-azetidinyl; each $R^7$ is independently selected from the group consisting of $C_1$-$C_6$alkyl, $C_3$-$C_6$cycloalkyl, $C_1$-$C_3$alkoxy$C_1$-$C_3$alkyl, $C_1$-$C_3$haloalkyl, halogen, N—$C_1$-$C_3$alkylamino, N.N-di$C_1$-$C_3$alkylamino, $C_1$-$C_3$haloalkoxy and $C_1$-$C_3$alkoxy; $R^9$ is selected from the group consisting of $C_1$-$C_3$alkyl, $C_1$-$C_3$alkoxy, $C_3$-$C_6$cycloalkyl, heterocyclyl, phenyl and a monocyclic heteroaryl, wherein said heterocyclyl, said phenyl and said monocyclic heteroaryl are optionally substituted with one or two $R^8$; and each $R^8$ is independently selected from the group consisting of halogen, $C_1$-$C_3$haloalkyl and $C_1$-$C_3$alkyl.

In one embodiment, described herein is a method of inhibiting transmission of a virus, a method of inhibiting viral entry, a method of inhibiting viral replication, a method of minimizing expression of viral proteins, or a method of inhibiting virus release, comprising administering a therapeutically effective amount of a compound of Formula I or pharmaceutically acceptable salt, stereoisomer, or tautomer thereof, to a patient suffering from the virus, and/or contacting an effective amount of a compound of Formula I or pharmaceutically acceptable salt, stereoisomer, or tautomer thereof, with a virally infected cell, wherein the compound of Formula I is represented by:

Formula I

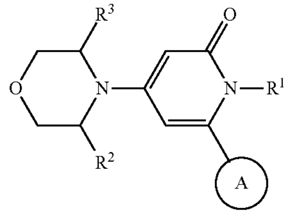

or a pharmaceutically acceptable salt, stereoisomer, or tautomer thereof, wherein: $R^1$, $R^2$, and $R^3$ are independently selected from the group consisting of H, $C_1$-$C_3$haloalkyl, and $C_1$-$C_3$alkyl; A represents:

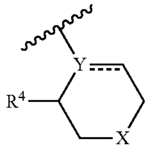

,

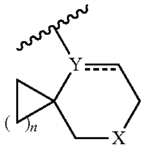

, or

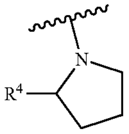

;

- - - is a single bond or a double bond; X is selected from the group consisting of $CH_2$, S, SO, $SO_2$, $NR^5$, $NCOR^5$, $NCOR^9$, $NCOCH_2R^9$, O, and a bond; Y is selected from the group consisting of N, CH, and C, provided that, when Y is CH, - - - is a single bond; n is selected from 1, 2, 3 and 4; each $R^4$ is independently selected from the group consisting of H, halogen, $COR^6$, $C_1$-$C_6$alkyl, $C_1$-$C_3$alkoxy$C_1$-$C_3$alkyl, $C_1$-$C_6$alkoxy, $C_3$-$C_6$cycloalkyl, $C_3$-$C_6$heterocyclyl, $C_1$-$C_3$cyanoalkyl, $C_1$-$C_3$haloalkyl, aryl, and heteroaryl, wherein said aryl and said heteroaryl are optionally substituted with one or more $R^7$; $R^5$ is selected from the group consisting of H, $C_1$-$C_3$fluoroalkyl, $C_1$-$C_3$alkyl, $C_1$-$C_3$alkoxy$C_1$-$C_3$alkyl, and $C_3$-$C_6$cycloalkyl; $R^6$ is selected from the group consisting of $C_1$-$C_3$alkoxy, N—$C_1$-$C_3$alkylamino, N.N-di$C_1$-$C_3$alkylamino, 1-pyrrolidinyl, 1-piperidinyl, and 1-azetidinyl; each $R^7$ is independently selected from the group consisting of $C_1$-$C_6$alkyl, $C_3$-$C_6$cycloalkyl, $C_1$-$C_3$alkoxy$C_1$-$C_3$alkyl, $C_1$-$C_3$haloalkyl, halogen, N—$C_1$-$C_3$alkylamino, N.N-di$C_1$-$C_3$alkylamino, $C_1$-$C_3$haloalkoxy and $C_1$-$C_3$alkoxy; $R^9$ is selected from the group consisting of $C_1$-$C_3$alkyl, $C_1$-$C_3$alkoxy, $C_3$-$C_6$cycloalkyl, heterocyclyl, phenyl and a monocyclic heteroaryl, wherein said heterocyclyl, said phenyl and said monocyclic heteroaryl are optionally substituted with one or two $R^8$; and each $R^8$ is independently selected from the group consisting of halogen, $C_1$-$C_3$haloalkyl and $C_1$-$C_3$alkyl.

In one embodiment, described herein is a method of inhibiting transmission of a virus, a method of inhibiting viral entry, a method of inhibiting viral replication, a method of minimizing expression of viral proteins, or a method of inhibiting virus release, comprising administering a therapeutically effective amount of a compound of Formula I or pharmaceutically acceptable salt, stereoisomer, or tautomer thereof, to a patient suffering from the virus, and/or contacting an effective amount of a compound of Formula I or pharmaceutically acceptable salt, stereoisomer, or tautomer thereof, with a virally infected cell, wherein the compound of Formula I is represented by:

Formula I

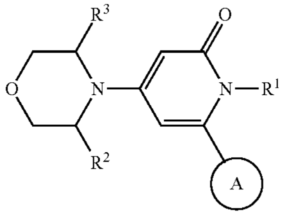

or a pharmaceutically acceptable salt, stereoisomer, or tautomer thereof, wherein: $R^1$, $R^2$, and $R^3$ are independently selected from the group consisting of H, $C_1$-$C_3$haloalkyl, and $C_1$-$C_3$alkyl; A represents:

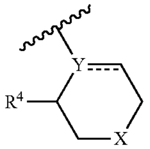

or

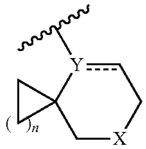

;

$\overline{---}$ is a single bond or a double bond; X is selected from the group consisting of $CH_2$, S, SO, $SO_2$, $NR^5$, $NCOR^5$, $NCOR^9$, $NCOCH_2R^9$, O, and a bond; Y is selected from the group consisting of N, CH, and C, provided that, when Y is CH, $\overline{---}$ is a single bond; n is selected from 1, 2, 3 and 4; $R^4$ is selected from the group consisting of H, halogen, $COR^6$, $C_1$-$C_6$alkyl, $C_1$-$C_3$alkoxy$C_1$-$C_3$alkyl, $C_1$-$C_6$alkoxy, $C_3$-$C_6$cycloalkyl, $C_3$-$C_6$heterocyclyl, $C_1$-$C_3$cyanoalkyl, $C_1$-$C_3$haloalkyl, aryl, and heteroaryl, wherein said aryl and said heteroaryl are optionally substituted with one or more $R^7$; $R^5$ is selected from the group consisting of H, $C_1$-$C_3$fluoroalkyl, $C_1$-$C_3$alkyl, $C_1$-$C_3$alkoxy$C_1$-$C_3$alkyl, and $C_3$-$C_6$cycloalkyl; $R^6$ is selected from the group consisting of $C_1$-$C_3$alkoxy, N—$C_1$-$C_3$alkylamino, N.N-di$C_1$-$C_3$alkylamino, 1-pyrrolidinyl, 1-piperidinyl, and 1-azetidinyl; each $R^7$ is independently selected from the group consisting of $C_1$-$C_6$alkyl, $C_3$-$C_6$cycloalkyl, $C_1$-$C_3$alkoxy$C_1$-$C_3$alkyl, $C_1$-$C_3$haloalkyl, halogen, N—$C_1$-$C_3$alkylamino, N.N-di$C_1$-$C_3$alkylamino, $C_1$-$C_3$haloalkoxy and $C_1$-$C_3$alkoxy; $R^9$ is selected from the group consisting of $C_1$-$C_3$alkyl, $C_1$-$C_3$alkoxy, $C_3$-$C_6$cycloalkyl, heterocyclyl, phenyl and a monocyclic heteroaryl, wherein said heterocyclyl, said phenyl and said monocyclic heteroaryl are optionally substituted with one or two $R^8$; and each $R^8$ is independently selected from the group consisting of halogen, $C_1$-$C_3$haloalkyl and $C_1$-$C_3$alkyl.

In one embodiment, described herein is a method of treating a Coronaviridae infection in a patient in need thereof comprising administering to the patient a therapeutically effective amount of a compound represented by Formula I:

Formula I

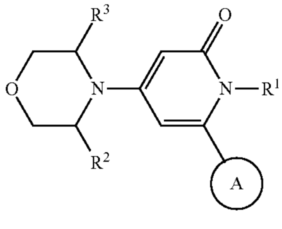

or a pharmaceutically acceptable salt, stereoisomer, or tautomer thereof, wherein: $R^1$, $R^2$, and $R^3$ are independently selected from the group consisting of H, $C_1$-$C_3$haloalkyl, and $C_1$-$C_3$alkyl; A represents:

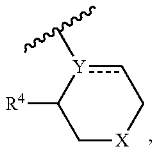

,

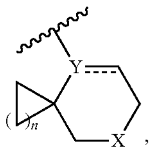

, or

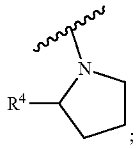

;

$\overline{---}$ is a single bond or a double bond; X is selected from the group consisting of $CH_2$, S, SO, $SO_2$, $NR^5$, $NCOR^5$, $NCOR^9$, $NCOCH_2R^9$, O, and a bond; Y is selected from the group consisting of N, CH, and C, provided that, when Y is CH, $\overline{---}$ is a single bond; n is selected from 1, 2, 3 and 4; each $R^4$ is independently selected from the group consisting of H, halogen, $COR^6$, $C_1$-$C_6$alkyl, $C_1$-$C_3$alkoxy$C_1$-$C_3$alkyl, $C_1$-$C_6$alkoxy, $C_3$-$C_6$cycloalkyl, $C_3$-$C_6$heterocyclyl, $C_1$-$C_3$cyanoalkyl, $C_1$-$C_3$haloalkyl, aryl, and heteroaryl, wherein said aryl and said heteroaryl are optionally substituted with one or more $R^7$; $R^5$ is selected from the group consisting of H, $C_1$-$C_3$fluoroalkyl, $C_1$-$C_3$alkyl, $C_1$-$C_3$alkoxy$C_1$-$C_3$alkyl, and $C_3$-$C_6$cycloalkyl; $R^6$ is selected from the group consisting of $C_1$-$C_3$alkoxy, N—$C_1$-$C_3$alkylamino, N.N-di$C_1$-$C_3$alkylamino, 1-pyrrolidinyl, 1-piperidinyl, and 1-azetidinyl; each $R^7$ is independently selected from the group consisting of $C_1$-$C_6$alkyl, $C_3$-$C_6$cycloalkyl, $C_1$-$C_3$alkoxy$C_1$-$C_3$alkyl, $C_1$-$C_3$haloalkyl, halogen, N—$C_1$-$C_3$alkylamino, N.N-di$C_1$-$C_3$alkylamino, $C_1$-$C_3$haloalkoxy and $C_1$-$C_3$alkoxy; $R^9$ is selected from the group consisting of $C_1$-$C_3$alkyl, $C_1$-$C_3$alkoxy, $C_3$-$C_6$cycloalkyl, heterocyclyl, phenyl and a monocyclic heteroaryl, wherein said heterocyclyl, said phenyl and said monocyclic heteroaryl are optionally substituted with one or two $R^8$; and each $R^8$ is independently selected from the group consisting of halogen, $C_1$-$C_3$haloalkyl and $C_1$-$C_3$alkyl.

In one embodiment, described herein is a method of treating a Coronaviridae infection in a patient in need thereof comprising administering to the patient a therapeutically effective amount of a compound represented by Formula I:

Formula I

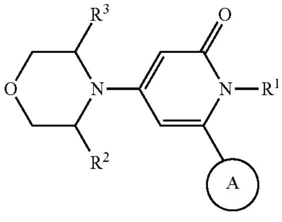

or a pharmaceutically acceptable salt, stereoisomer, or tautomer thereof, wherein: $R^1$, $R^2$, and $R^3$ are independently selected from the group consisting of H, $C_1$-$C_3$haloalkyl, and $C_1$-$C_3$alkyl; A represents:

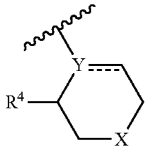 or 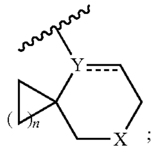 ;

$\overline{---}$ is a single bond or a double bond; X is selected from the group consisting of $CH_2$, S, SO, $SO_2$, $NR^5$, $NCOR^5$, $NCOR^9$, $NCOCH_2R^9$, O, and a bond; Y is selected from the group consisting of N, CH, and C, provided that, when Y is CH, $\overline{---}$ is a single bond; n is selected from 1, 2, 3 and 4; $R^4$ is selected from the group consisting of H, halogen, $COR^6$, $C_1$-$C_6$alkyl, $C_1$-$C_3$alkoxy$C_1$-$C_3$alkyl, $C_1$-$C_6$alkoxy, $C_3$-$C_6$cycloalkyl, $C_3$-$C_6$heterocyclyl, $C_1$-$C_3$cyanoalkyl, $C_1$-$C_3$haloalkyl, aryl, and heteroaryl, wherein said aryl and said heteroaryl are optionally substituted with one or more $R^7$; $R^5$ is selected from the group consisting of H, $C_1$-$C_3$fluoroalkyl, $C_1$-$C_3$alkyl, $C_1$-$C_3$alkoxy$C_1$-$C_3$alkyl, and $C_3$-$C_6$cycloalkyl; $R^6$ is selected from the group consisting of $C_1$-$C_3$alkoxy, N—$C_1$-$C_3$alkylamino, N.N-di$C_1$-$C_3$alkylamino, 1-pyrrolidinyl, 1-piperidinyl, and 1-azetidinyl; each $R^7$ is independently selected from the group consisting of $C_1$-$C_6$alkyl, $C_3$-$C_6$cycloalkyl, $C_1$-$C_3$alkoxy$C_1$-$C_3$alkyl, $C_1$-$C_3$haloalkyl, halogen, N—$C_1$-$C_3$alkylamino, N.N-di$C_1$-$C_3$alkylamino, $C_1$-$C_3$haloalkoxy and $C_1$-$C_3$alkoxy; $R^9$ is selected from the group consisting of $C_1$-$C_3$alkyl, $C_1$-$C_3$alkoxy, $C_3$-$C_6$cycloalkyl, heterocyclyl, phenyl and a monocyclic heteroaryl, wherein said heterocyclyl, said phenyl and said monocyclic heteroaryl are optionally substituted with one or two $R^8$; and each $R^8$ is independently selected from the group consisting of halogen, $C_1$-$C_3$haloalkyl and $C_1$-$C_3$alkyl.

DETAILED DESCRIPTION

Figure 1:
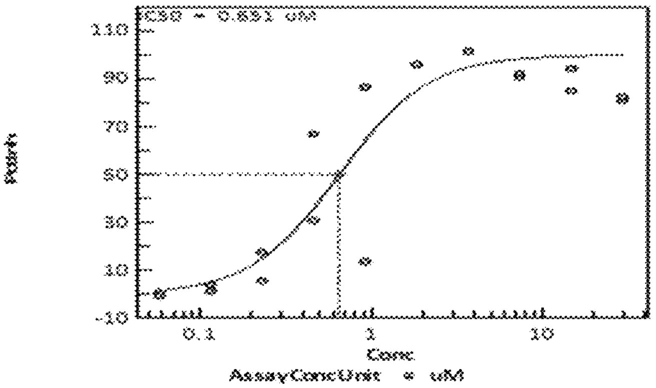
FIG. 1 depicts exemplary dose response of Compound 1 for inhibition of SARS CoV-1 mediated cell killing.

The definitions set forth in this application are intended to clarify terms used throughout this application. Unless defined otherwise, all technical and scientific terms used herein have the same meaning as is commonly understood by one of skill in art to which the subject matter herein belongs. As used in the specification and the appended claims, unless specified to the contrary, the following terms have the meaning indicated in order to facilitate the understanding of the present disclosure. When a substituent is listed without indicating the atom via which such substituent is bonded to the rest of the compound of a given formula, then such substituent may be bonded via any atom in such substituent. Combinations of substituents, positions of substituents and/or variables are permissible only if such combinations result in stable compounds. It is understood that substituents and substitution patterns on the compounds of the present disclosure can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, "Compound 1" refers to a compound having the structure:

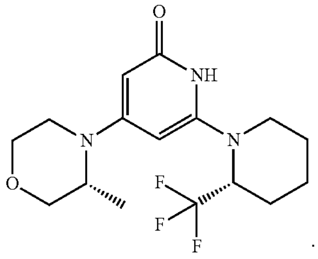 [SMILES: C[C@@H]1COCCN1c1cc(N2CCCC[C@@H]2C(F)(F)F)[nH]c(=O)c1].

As used herein, "Compound 2" refers to a compound having the structure:

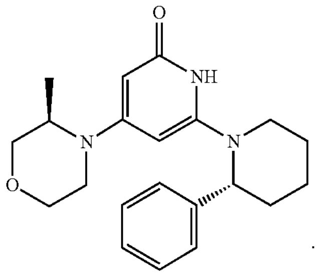 [SMILES: C[C@@H]1COCCN1c1cc(N2CCCC[C@@H]2c2ccccc2)[nH]c(=O)c1].

As used herein, "Compound 3" refers to a compound having the structure:

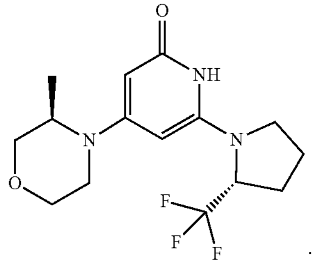 [SMILES: C[C@@H]1COCCN1c1cc(N2CCC[C@@H]2C(F)(F)F)[nH]c(=O)c1].

As used herein, "Compound 4" refers to a compound having the structure:

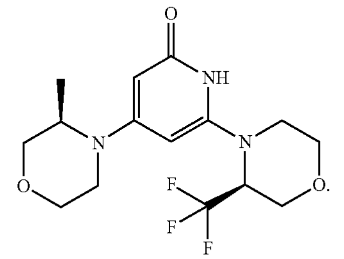 [SMILES: C[C@@H]1COCCN1c1cc(N2CCOC[C@H]2C(F)(F)F)[nH]c(=O)c1]

As used herein, "Compound 5" refers to a compound having the structure:

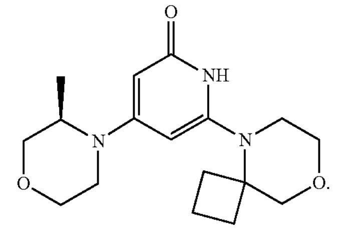 [SMILES: C[C@@H]1COCCN1c1cc(N2CCOCC23CCC3)[nH]c(=O)c1]

As used herein, the term "$C_1$-$C_6$alkyl" means both linear and branched chain saturated hydrocarbon groups with 1 to 6 carbon atoms. Examples of $C_1$-$C_6$alkyl groups include methyl, ethyl, n-propyl, isopropyl, n-butyl, iso-butyl, sec-butyl, t-butyl, n-pentyl, 4-methyl-butyl, n-hexyl, 2-ethyl-butyl groups. Among unbranched $C_1$-$C_6$alkyl groups, typical ones are methyl, ethyl, n-propyl, n-butyl, n-pentyl and n-hexyl groups. Among branched alkyl groups, there may be mentioned iso-propyl, iso-butyl, sec-butyl, t-butyl, 4-methyl-butyl and 2-ethyl-butyl groups.

As used herein, the term "$C_1$-$C_3$alkyl" means both linear and branched chain saturated hydrocarbon groups with 1 to 3 carbon atoms. Examples of $C_1$-$C_3$alkyl groups include methyl, ethyl, n-propyl and isopropyl groups.

As used herein, the term "$C_1$-$C_6$alkoxy" means the group O-alkyl, where "$C_1$-$C_6$alkyl" is used as described above. Examples of $C_1$-$C_6$alkoxy groups include, but are not limited to, methoxy, ethoxy, isopropoxy, n-propoxy, n-butoxy, n-hexoxy, 3-methyl-butoxy groups.

As used herein, the term "$C_1$-$C_3$alkoxy" means the group O-alkyl, where "$C_1$-$C_3$alkyl" is used as described above. Examples of $C_1$-$C_3$alkoxy groups include, but are not limited to, methoxy, ethoxy, isopropoxy and n-propoxy.

As used herein, the term "$C_1$-$C_6$haloalkyl" means both linear and branched chain saturated hydrocarbon groups, with 1 to 6 carbon atoms and with 1 to all hydrogens substituted by a halogen of different or same type. Examples of $C_1$-$C_6$haloalkyl groups include methyl substituted with 1 to 3 halogen atoms, ethyl substituted with 1 to 5 halogen atoms, n-propyl or iso-propyl substituted with 1 to 7 halogen atoms, n-butyl or iso-butyl substituted with 1 to 9 halogen atoms, and sec-butyl or t-butyl groups substituted with 1 to 9 halogen atoms.

As used herein, the term "$C_1$-$C_3$haloalkyl" means both linear and branched chain saturated hydrocarbon groups, with 1 to 3 carbon atoms and with 1 to all hydrogens substituted by a halogen of different or same type. Examples of $C_1$-$C_3$haloalkyl groups include methyl substituted with 1 to 3 halogen atoms, ethyl substituted with 1 to 5 halogen atoms, and n-propyl or iso-propyl substituted with 1 to 7 halogen atoms.

As used herein, the term "$C_1$-$C_3$haloalkoxy" means both linear and branched chain saturated alkoxy groups, with 1 to 3 carbon atoms and with 1 to all hydrogen atoms substituted by a halogen atom of different or same type. Examples of $C_1$-$C_3$haloalkoxy groups include methoxy substituted with 1 to 3 halogen atoms, ethoxy substituted with 1 to 5 halogen atoms, and n-propoxy or iso-propoxy substituted with 1 to 7 halogen atoms.

As used herein, the term "$C_1$-$C_3$fluorooalkyl" means both linear and branched chain saturated hydrocarbon groups, With 1 to 3 carbon atoms and with 1 to all hydrogen atoms substituted by a fluorine atom. Examples of $C_1$-$C_3$fluoroalkyl groups include methyl substituted with 1 to 3 fluorine atoms, ethyl substituted with 1 to 5 fluorine atoms, and n-propyl or iso-propyl substituted with 1 to 7 fluorine atoms.

As used herein, the term "$C_1$-$C_3$fluorooalkoxy" means both linear and branched chain saturated alkoxy groups, with 1 to 3 carbon atoms and with 1 to all hydrogen atoms substituted by a fluorine atom. Examples of $C_1$-$C_3$fluoroalkoxy groups include methoxy substituted with 1 to 3 fluorine atoms, ethoxy substituted with 1 to 5 fluorine atoms, and n-propoxy or iso-propoxy substituted with 1 to 7 fluorine atoms.

As used herein, the term "$C_3$-$C_6$cycloalkyl" means a cyclic saturated hydrocarbon group, with 3 to 6 carbon atoms. Examples of $C_3$-$C_6$cycloalkyl groups include cyclopropyl, cyclobutyl, cyclopentyl and cyclohexyl.

As used herein, the term "$C_1$-$C_3$alkoxy$C_1$-$C_3$alkyl" means both a both linear and branched chain saturated hydrocarbon group, with 1 to 3 carbon atoms, substituted with an alkoxy group with 1 to 3 carbon atoms. Examples of $C_1$-$C_3$alkoxy$C_1$-$C_3$alkyl groups are drawn below.

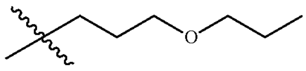
,
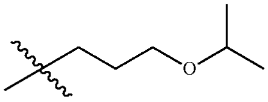
,
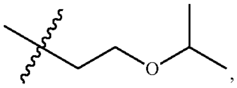
,
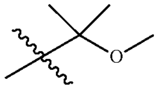

As used herein, the term "$C_1$-$C_3$cyanoalkyl" means both a linear and branched chain cyano (CN) derivative, with one to three carbon atoms including the carbon atom that is part of the cyano group. Examples of $C_1$-$C_3$cyanoalkyl groups are drawn below.

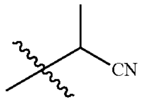 [SMILES: *C(C)C#N]

As used herein, the term "halogen" means fluorine, chlorine, bromine or iodine.

As used herein, the term "aryl" means a monocyclic or bicyclic aromatic carbocyclic group. Examples of aryl groups include phenyl and naphthyl. A naphthyl group may be attached through the 1 or the 2 position. In a bicyclic aryl, one of the rings may be partially saturated. Examples of such groups include indanyl and tetrahydronaphthyl.

As used herein, the term "monocyclic aryl" means a monocyclic aromatic carbocyclic group. Examples of monocyclic aryl groups include phenyl.

As used herein, the term "heteroaryl" means a monocyclic or bicyclic aromatic group of carbon atoms wherein from one to three of the carbon atoms is/are replaced by one or more heteroatoms independently selected from nitrogen, oxygen or sulfur. In a bicyclic aryl, one of the rings may be partially saturated. Examples of such groups include indolinyl, dihydrobenzofuran and 1,3-benzodioxolyl.

As used herein, the term "monocyclic heteroaryl" means a monocyclic aromatic group of carbon atoms wherein from one to three of the carbon atoms is/are replaced by one or more heteroatoms independently selected from nitrogen, oxygen or sulfur.

Examples of monocyclic heteroaryl groups include, but are not limited to, furyl, thienyl, pyrrolyl, oxazolyl, thiazolyl, imidazolyl, oxadiazolyl, thiadiazolyl, pyridyl, triazolyl, triazinyl, pyridazyl, isothiazolyl, isoxazolyl, pyrazinyl, pyrazolyl, and pyrimidinyl.

Examples of bicyclic heteroaryl groups include, but are not limited to, quinoxalinyl, quinazolinyl, pyridopyrazinyl, benzoxazolyl, benzothiophenyl, benzimidazolyl, naphthyridinyl, quinolinyl, benzofuryl, indolyl, indazolyl, benzothiazolyl, pyridopyrimidinyl, and isoquinolinyl.

As used herein, the term "heterocyclyl" means a cyclic group of carbon atoms wherein from one to three of the carbon atoms is/are replaced by one or more heteroatoms independently selected from nitrogen, oxygen and sulfur. Examples of heterocyclyl groups include, but are not limited to, tetrahydrofuryl, tetrahydropyranyl, pyrrolidinyl, piperidinyl, piperazinyl, morpholinyl and dioxanyl.

A "combination therapy" is a treatment that includes the administration of two or more therapeutic agents, e.g., a compound of Formula I and an antibiotic, a viral protease inhibitor, or an anti-viral nucleoside anti-metabolite, to a patient in need thereof.

"Disease," "disorder," and "condition" are used interchangeably herein.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds described herein can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like).

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The presently described compounds encompasses various stereoisomers of these compounds and mixtures thereof. Mixtures of enantiomers or diastereomers may be designated "(±)" in nomenclature, but the skilled artisan will recognize that a structure may denote a chiral center implicitly.

In the present specification, the term "therapeutically effective amount" means the amount of the subject compound that will elicit the biological or medical response of a tissue, system or animal, (e.g., mammal or human) that is being sought by the researcher, veterinarian, medical doctor or other clinician. The compounds described herein are administered in therapeutically effective amounts to treat a disorder.

"Treating" includes any effect, e.g., lessening, reducing, modulating, or eliminating, that results in the improvement of the condition, disease, disorder and the like.

The disclosure also embraces isotopically labeled compounds which are identical to those recited herein, except that one or more atoms are replaced by an atom having an atomic mass or mass number different from the atomic mass or mass number usually found in nature. Examples of isotopes that can be incorporated into compounds of the present disclosure include isotopes of hydrogen, carbon, nitrogen, oxygen, phosphorus, sulfur, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the disclosure may have one or more H atom replaced with deuterium.

Individual enantiomers and diastereomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009.

Compounds

In one embodiment, described herein is a compound of Formula I:

Formula I

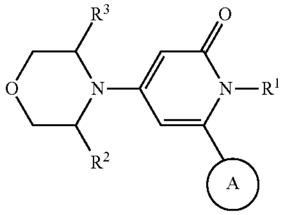

or a pharmaceutically acceptable salt, stereoisomer, or tautomer thereof, wherein: $R^1$, $R^2$, and $R^3$ are independently selected from the group consisting of H, $C_1$-$C_3$haloalkyl, and $C_1$-$C_3$alkyl; A represents:

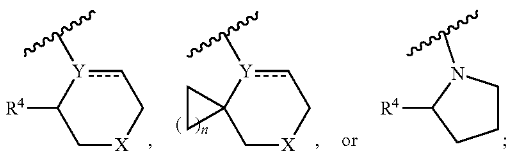

$\overline{---}$ is a single bond or a double bond; X is selected from the group consisting of $CH_2$, S, SO, $SO_2$, $NR^5$, $NCOR^5$, $NCOR^9$, $NCOCH_2R^9$, O, and a bond; Y is selected from the group consisting of N, CH, and C, provided that, when Y is CH, $\overline{---}$ is a single bond; n is selected from 1, 2, 3 and 4; each $R^4$ is independently selected from the group consisting of H, halogen, $COR^6$, $C_1$-$C_6$alkyl, $C_1$-$C_3$alkoxy$C_1$-$C_3$alkyl, $C_1$-$C_6$alkoxy, $C_3$-$C_6$cycloalkyl, $C_3$-$C_6$heterocyclyl, $C_1$-$C_3$cyanoalkyl, $C_1$-$C_3$haloalkyl, aryl, and heteroaryl, wherein said aryl and said heteroaryl are optionally substituted with one or more $R^7$; $R^5$ is selected from the group consisting of H, $C_1$-$C_3$fluoroalkyl, $C_1$-$C_3$alkyl, $C_1$-$C_3$alkoxy$C_1$-$C_3$alkyl, and $C_3$-$C_6$cycloalkyl; $R^6$ is selected from the group consisting of $C_1$-$C_3$alkoxy, N—$C_1$*$C_3$alkylamino, N.N-di$C_1$-$C_3$alkylamino, 1-pyrrolidinyl, 1-piperidinyl, and 1-azetidinyl; each $R^7$ is independently selected from the group consisting of $C_1$-$C_6$alkyl, $C_3$-$C_6$cycloalkyl, $C_1$-$C_3$alkoxy$C_1$-$C_3$alkyl, $C_1$-$C_3$haloalkyl, halogen, N—$C_1$-$C_3$alkylamino, N.N-di$C_1$-$C_3$alkylamino, $C_1$-$C_3$haloalkoxy and $C_1$-$C_3$alkoxy; $R^9$ is selected from the group consisting of $C_1$-$C_3$alkyl, $C_1$-$C_3$alkoxy, $C_3$-$C_6$cycloalkyl, heterocyclyl, phenyl and a monocyclic heteroaryl, wherein said heterocyclyl, said phenyl and said monocyclic heteroaryl are optionally substituted with one or two $R^8$; and each $R^8$ is independently selected from the group consisting of halogen, $C_1$-$C_3$haloalkyl and $C_1$-$C_3$alkyl.

In one embodiment, described herein is a compound of Formula I:

Formula I

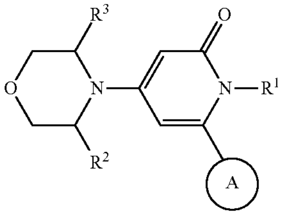

or a pharmaceutically acceptable salt, stereoisomer, or tautomer thereof, wherein: $R^1$, $R^2$, and $R^3$ are independently selected from the group consisting of H, $C_1$-$C_3$haloalkyl, and $C_1$-$C_3$alkyl; A represents:

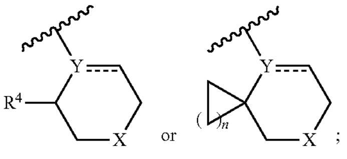

$\overline{---}$ is a single bond or a double bond; X is selected from the group consisting of $CH_2$, S, SO, 502, $NR^5$, $NCOR^5$, $NCOR^9$, $NCOCH_2R^9$, O, and a bond; Y is selected from the group consisting of N, CH, and C, provided that, when Y is CH, $\overline{---}$ is a single bond; n is selected from 1, 2, 3 and 4; $R^4$ is selected from the group consisting of H, halogen, $COR^6$, $C_1$-$C_6$alkyl, $C_1$-$C_3$alkoxy$C_1$-$C_3$alkyl, $C_1$-$C_6$alkoxy, $C_3$-$C_6$cycloalkyl, $C_3$-$C_6$heterocyclyl, $C_1$-$C_3$cyanoalkyl, $C_1$-$C_3$haloalkyl, aryl, and heteroaryl, wherein said aryl and said heteroaryl are optionally substituted with one or more $R^7$; $R^5$ is selected from the group consisting of H, $C_1$-$C_3$fluoroalkyl, $C_1$-$C_3$alkyl, $C_1$-$C_3$alkoxy$C_1$-$C_3$alkyl, and $C_3$-$C_6$cycloalkyl; $R^6$ is selected from the group consisting of $C_1$-$C_3$alkoxy, N—$C_1$-$C_3$alkylamino, N.N-di$C_1$-$C_3$alkylamino, 1-pyrrolidinyl, 1-piperidinyl, and 1-azetidinyl; each $R^7$ is independently selected from the group consisting of $C_1$-$C_6$alkyl, $C_3$-$C_6$cycloalkyl, $C_1$-$C_3$alkoxy$C_1$-$C_3$alkyl, $C_1$-$C_3$haloalkyl, halogen, N—$C_1$-$C_3$alkylamino, N.N-di$C_1$-$C_3$alkylamino, $C_1$-$C_3$haloalkoxy and $C_1$-$C_3$alkoxy; $R^9$ is selected from the group consisting of $C_1$-$C_3$alkyl, $C_1$-$C_3$alkoxy, $C_3$-$C_6$cycloalkyl, heterocyclyl, phenyl and a monocyclic heteroaryl, wherein said heterocyclyl, said phenyl and said monocyclic heteroaryl are optionally substituted with one or two $R^8$; and each $R^8$ is independently selected from the group consisting of halogen, $C_1$-$C_3$haloalkyl and $C_1$-$C_3$alkyl.

In some embodiments, $R^1$ is H. In some embodiments, $R^2$ is H. In some embodiments, $R^3$ is $C_1$-$C_3$alkyl. In some embodiments, A is piperidinyl. In some embodiments, $R^4$ is $C_1$-$C_3$haloalkyl. In some embodiments, n is 2.

In some embodiments, the compound is selected from the group consisting of: 4-morpholino-6-(2-phenylpyrrolidin-1-yl)-1H-pyridin-2-one; 1-methyl-4-morpholino-6-(2-phenylpyrrolidin-1-yl)pyridin-2-one; 4-morpholino-6-[(2S)-2-phenylpyrrolidin-1-yl]-1H-pyridin-2-one; 4-morpholino-6-[(2R)-2-phenylpyrrolidin-1-yl]-1H-pyridin-2-one; 6-(3,6-dihydro-2H-pyran-4-yl)-4-(3-methyl morpholin-4-yl)-1H-pyridin-2-one; 4-(3-methylmorpholin-4-yl)-6-tetrahydropyran-4-yl-1H-pyridin-2-one; 6-[2-(3-methoxyphenyl)pyrrolidin-1-yl]-4-(3-methylmorpholin-4-yl)-1H-pyridin-2-one; 4-(3-methylmorpholin-4-yl)-6-[2-(3-pyridyl)pyrrolidin-1-yl]-1H-pyridin-2-one; 4-(3-methylmorpholin-4-yl)-6-(2-phenylpyrrolidin-1-yl)-1H-pyridin-2-one; N,N-dimethyl-1-[4-[(3R)-3-methylmorpholin-4-yl]-6-oxo-1H-pyridin-2-yl]pyrrolidine-2-carboxamide; 6-[2-(1-methoxy-1-methyl-ethyl) pyrrolidin-1-yl]-4-[(3R)-3-methylmorpholin-4-yl]-1H-pyridin-2-one; 6-(2-cyclohexylpyrrolidin-1-yl)-4-[(3R)-3-methylmorpholin-4-yl]-1H-pyridin-2-one; 6-[2-(3-fluorophenyl)pyrrolidin-1-yl]-4-[(3R)-3-methylmorpholin-4-yl]-1H-pyridin-2-one; 6-[2-(2,5-difluorophenyl) pyrrolidin-1-yl]-4-[(3R)-3-methylmorpholin-4-yl]-1H-pyridin-2-one; 4-[(3R)-3-methylmorpholin-4-yl]-6-[2-[3-(trifluoromethoxy)phenyl]pyrrolidin-1-yl]-1H-pyridin-2-one; 4-[(3R)-3-methylmorpholin-4-yl]-6-[2-[3-(trifluoromethyl)phenyl]pyrrolidin-1-yl]-1H-pyridin-2-one; 6-[2-(3-methoxyphenyl)pyrrolidin-1-yl]-4-[(3R)-3-methylmorpholin-4-yl]-1H-pyridin-2-one; 4-[(3R)-3-methylmorpholin-4-yl]-6-(2-phenylpyrrolidin-1-yl)-1H-pyridin-2-one; 4-[(3R)-3-methylmorpholin-4-yl]-6-[2-(1-methylpyrazol-4-yl)pyrrolidin-1-yl]-1H-pyridin-2-one; 6-[2-(1,5-dimethylpyrazol-3-yl)pyrrolidin-1-yl]-4-[(3R)-3-methylmorpholin-4-yl]-1H-pyridin-2-one; 6-[2-(1-ethylpyrazol-3-yl) pyrrolidin-1-yl]-4-[(3R)-3-methylmorpholin-4-yl]-1H-pyridin-2-one; 6-[2-(5-methyl-2-furyl)pyrrolidin-1-yl]-4-[(3R)-3-methylmorpholin-4-yl]-1H-pyridin-2-one; 6-[2-[3-(dimethylamino)phenyl]pyrrolidin-1-yl]-4-[(3R)-3-methylmorpholin-4-yl]-1H pyridin-2-one; 4-[(3R)-3-methylmorpholin-4-yl]-6-(3-methylmorpholin-4-yl)-1H-pyridin-2-one; 4-[(3R)-3-methylmorpholin-4-yl]-6-[2-(trifluoromethyl)-1-piperidyl]-1H-pyridin-2-one; 4-[(3R)-3-methylmorpholin-4-yl]-6-(3-phenylmorpholin-4-yl)-1H-pyridin-2-one; 4-[(3R)-3-methylmorpholin-4-yl]-6-(1-oxo-1,4-thiazinan-4-yl)-1H-pyridin-2-one; 6-(1,1-dioxo-1,4-thiazinan-4-yl)-4-[(3R)-3-methylmorpholin-4-yl]-1H-pyridin-2-one; 6-(4-acetylpiperazin-1-yl)-4-[(3R)-3-methylmorpholin-4-yl]-1H-pyridin-2-one; 4-[(3R)-3-methylmorpholin-4-yl]-6-[(2R)-2-phenyl-1-piperidyl]-1H-pyridin-2-one; 4-[(3R)-3-methylmorpholin-4-yl]-6-(4-methyl-2-phenyl-piperazin-1-yl)-1H-pyridin-2-one; 4-[(3R)-3-methylmorpholin-4-yl]-6-[3-(trifluoromethyl) morpholin-4-yl]-1H-pyridin-2-one; 6-(3-cyclopropylmorpholin-4-yl)-4-[(3R)-3-methylmorpholin-4-yl]-1H-pyridin-2-one; 4-[(3R)-3-methylmorpholin-4-yl]-6-[(2S)-2-(trifluoromethyl)pyrrolidin-1-yl]-1H-pyridin-2-one; 4-[(3R)-3-methylmorpholin-4-yl]-6-[(2R)-2-(trifluoromethyl)pyrrolidin-1-yl]-1H-pyridin-2-one; 6-[2-(3-chlorophenyl)pyrrolidin-1-yl]-4-[(3R)-3-methylmorpholin-4-yl]-1H-pyridin-2-one; 6-[2-(3-cyclopropylphenyl)pyrrolidin-1-yl]-4-[(3R)-3-methylmorpholin-4-yl]-1H-pyridin-2-one; 4-[(3R)-3-methylmorpholin-4-yl]-6-[2-(2-pyridyl)pyrrolidin-1-yl]-1H-pyridin-2-one; 4-[(3R)-3-methylmorpholin-4-yl]-6-(2-thiazol-2-ylpyrrolidin-1-yl)-1H-pyridin-2-one; 6-[2-(5-methylisoxazol-3-yl)pyrrolidin-1-yl]-4-[(3R)-3-methylmorpholin-4-yl]-1H-pyridin-2-one; 1-methyl-4-[(3R)-3-methylmorpholin-4-yl]-6-[(2R)-2-(trifluoromethyl)-1-piperidyl]pyridin-2-one; 4-[(3R)-3-methylmorpholin-4-yl]-6-(8-oxa-5-azaspiro[3.5]nonan-5-yl)-1H-pyridin-2-one; 6-[2-(3-methoxyphenyl)-1-piperidyl]-4-[(3R)-3-methylmorpholin-4-yl]-1H-pyridin-2-one; 6-[4-acetyl-2-(trifluoromethyl)piperazin-1-yl]-4-[(3R)-3-methylmorpholin-4-yl]-1H pyridin-2-one; 6-[4-(5-fluoropyridine-3-carbonyl)-2-(trifluoromethyl)piperazin-1-yl]-4-[(3R)-3-methylmorpholin-4-yl]-1H-pyridin-2-one; 6-[4-[2-(4-fluorophenyl)acetyl]-2-(trifluoromethyl)piperazin-1-yl]-4-[(3R)-3-methylmorpholin-4-yl]-1H-pyridin-2-one; 4-[(3R)-3-methylmorpholin-4-yl]-6-[4-(tetrahydrofuran-2-carbonyl)-2-(trifluoromethyl)piperazin-1-yl]-1H-pyridin-2-one; and 4-[(3R)-3-methylmorpholin-4-yl]-6-[4-methyl-2-(trifluoromethyl)piperazin-1-yl]-1H-pyridin-2-one; and pharmaceutically acceptable salts, stereoisomers, and tautomers thereof.

In some embodiments, the compound is selected from the group consisting of:

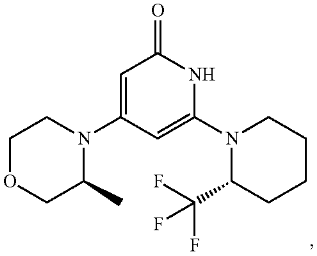
,

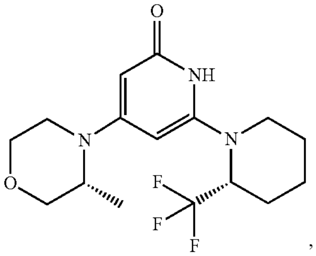
,

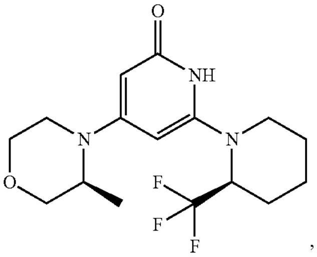
,

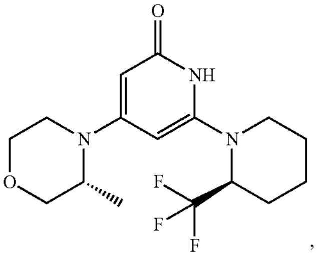
, and pharmaceutically acceptable salts, stereoisomers, and tautomers thereof.

In some embodiments, the compound is selected from the group consisting of:

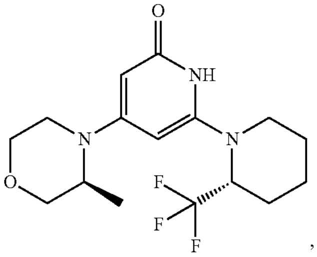

,

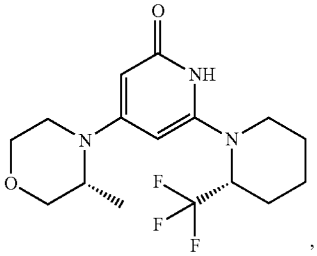

,

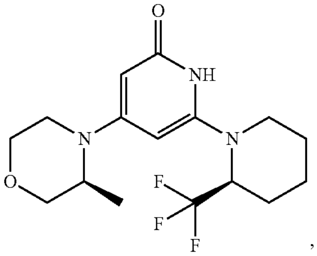

,

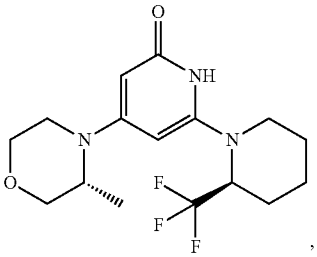

, and pharmaceutically acceptable salts thereof.

In some embodiments, the compound is selected from the group consisting of:

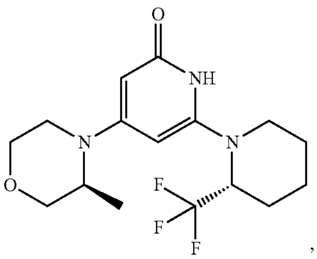

,

-continued

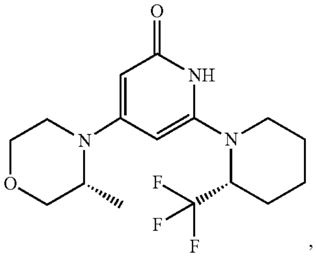

, and pharmaceutically acceptable salts thereof.

In some embodiments, the compound is selected from the group consisting of:

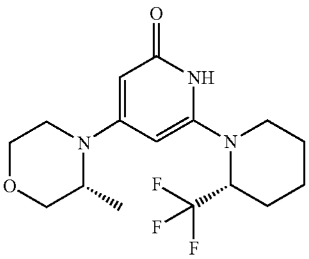 [SMILES: C[C@@H]1COCCN1c1cc(N2CCCC[C@@H]2C(F)(F)F)[nH]c(=O)c1]

and pharmaceutically acceptable salts thereof.

Methods of Treatment

In one embodiment, described herein is a method of ameliorating or treating a viral infection in a patient in need thereof, comprising administering to the patient a therapeutically effective amount of a compound represented by Formula I:

Formula I

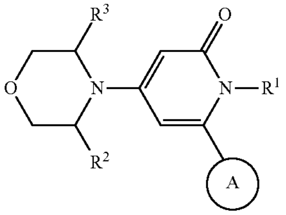

or a pharmaceutically acceptable salt, stereoisomer, or tautomer thereof, wherein: $R^1$, $R^2$, and $R^3$ are independently selected from the group consisting of H, $C_1$-$C_3$haloalkyl, and $C_1$-$C_3$alkyl; A represents:

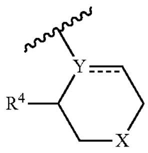

,

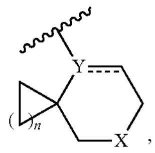

, or

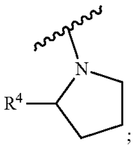

;

⎓ is a single bond or a double bond; X is selected from the group consisting of $CH_2$, S, SO, $SO_2$, $NR^5$, $NCOR^5$, $NCOR^9$, $NCOCH_2R^9$, O, and a bond; Y is selected from the group consisting of N, CH, and C, provided that, when Y is CH, ⎓ is a single bond; n is selected from 1, 2, 3 and 4; each $R^4$ is independently selected from the group consisting of H, halogen, $COR^6$, $C_1$-$C_6$alkyl, $C_1$-$C_3$alkoxy$C_1$-$C_3$alkyl, $C_1$-$C_6$alkoxy, $C_3$-$C_6$cycloalkyl, $C_3$-$C_6$heterocyclyl, $C_1$-$C_3$cyanoalkyl, $C_1$-$C_3$haloalkyl, aryl, and heteroaryl, wherein said aryl and said heteroaryl are optionally substituted with one or more $R^7$; $R^5$ is selected from the group consisting of H, $C_1$-$C_3$fluoroalkyl, $C_1$-$C_3$alkyl, $C_1$-$C_3$alkoxy$C_1$-$C_3$alkyl, and $C_3$-$C_6$cycloalkyl; $R^6$ is selected from the group consisting of $C_1$-$C_3$alkoxy, N—$C_1$-$C_3$alkylamino, N.N-di$C_1$-$C_3$alkylamino, 1-pyrrolidinyl, 1-piperidinyl, and 1-azetidinyl; each $R^7$ is independently selected from the group consisting of $C_1$-$C_6$alkyl, $C_3$-$C_6$cycloalkyl, $C_1$-$C_3$alkoxy$C_1$-$C_3$alkyl, $C_1$-$C_3$haloalkyl, halogen, N—$C_1$-$C_3$alkylamino, N.N-di$C_1$-$C_3$alkylamino, $C_1$-$C_3$haloalkoxy and $C_1$-$C_3$alkoxy; $R^9$ is selected from the group consisting of $C_1$-$C_3$alkyl, $C_1$-$C_3$alkoxy, $C_3$-$C_6$cycloalkyl, heterocyclyl, phenyl and a monocyclic heteroaryl, wherein said heterocyclyl, said phenyl and said monocyclic heteroaryl are optionally substituted with one or two $R^8$; and each $R^8$ is independently selected from the group consisting of halogen, $C_1$-$C_3$haloalkyl and $C_1$-$C_3$alkyl.

In one embodiment, described herein is a method of ameliorating or treating a viral infection in a patient in need thereof, comprising administering to the patient a therapeutically effective amount of a compound represented by Formula I:

Formula I

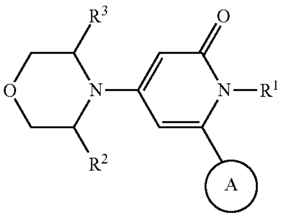

or a pharmaceutically acceptable salt, stereoisomer, or tautomer thereof, wherein: $R^1$, $R^2$, and $R^3$ are independently selected from the group consisting of H, $C_1$-$C_3$haloalkyl, and $C_1$-$C_3$alkyl; A represents:

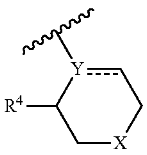

or

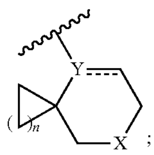

;

$\overline{- - -}$ is a single bond or a double bond; X is selected from the group consisting of $CH_2$, S, SO, $SO_2$, $NR^5$, $NCOR^5$, $NCOR^9$, $NCOCH_2R^9$, O, and a bond; Y is selected from the group consisting of N, CH, and C, provided that, when Y is CH, $\overline{- - -}$ is a single bond; n is selected from 1, 2, 3 and 4; $R^4$ is selected from the group consisting of H, halogen, $COR^6$, $C_1$-$C_6$alkyl, $C_1$-$C_3$alkoxy$C_1$-$C_3$alkyl, $C_1$-$C_6$alkoxy, $C_3$-$C_6$cycloalkyl, $C_3$-$C_6$heterocyclyl, $C_1$-$C_3$cyanoalkyl, $C_1$-$C_3$haloalkyl, aryl, and heteroaryl, wherein said aryl and said heteroaryl are optionally substituted with one or more $R^7$; $R^5$ is selected from the group consisting of H, $C_1$-$C_3$fluoroalkyl, $C_1$-$C_3$alkyl, $C_1$-$C_3$alkoxy$C_1$-$C_3$alkyl, and $C_3$-$C_6$cycloalkyl; $R^6$ is selected from the group consisting of $C_1$-$C_3$alkoxy, N—$C_1$-$C_3$alkylamino, N.N-di$C_1$-$C_3$alkylamino, 1-pyrrolidinyl, 1-piperidinyl, and 1-azetidinyl; each $R^7$ is independently selected from the group consisting of $C_1$-$C_6$alkyl, $C_3$-$C_6$cycloalkyl, $C_1$-$C_3$alkoxy$C_1$-$C_3$alkyl, $C_1$-$C_3$haloalkyl, halogen, N—$C_1$-$C_3$alkylamino, N.N-di$C_1$-$C_3$alkylamino, $C_1$-$C_3$haloalkoxy and $C_1$-$C_3$alkoxy; $R^9$ is selected from the group consisting of $C_1$-$C_3$alkyl, $C_1$-$C_3$alkoxy, $C_3$-$C_6$cycloalkyl, heterocyclyl, phenyl and a monocyclic heteroaryl, wherein said heterocyclyl, said phenyl and said monocyclic heteroaryl are optionally substituted with one or two $R^8$; and each $R^8$ is independently selected from the group consisting of halogen, $C_1$-$C_3$haloalkyl and $C_1$-$C_3$alkyl.

In one embodiment, described herein is a method of inhibiting transmission of a virus, a method of inhibiting viral entry, a method of inhibiting viral replication, a method of minimizing expression of viral proteins, or a method of inhibiting virus release, comprising administering a therapeutically effective amount of a compound of Formula I or pharmaceutically acceptable salt, stereoisomer, or tautomer thereof, to a patient suffering from the virus, and/or contacting an effective amount of a compound of Formula I or pharmaceutically acceptable salt, stereoisomer, or tautomer thereof, with a virally infected cell, wherein the compound of Formula I is represented by:

Formula I

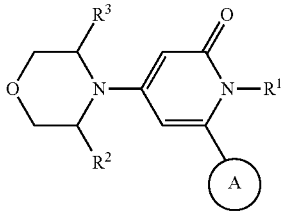

or a pharmaceutically acceptable salt, stereoisomer, or tautomer thereof, wherein: $R^1$, $R^2$, and $R^3$ are independently selected from the group consisting of H, $C_1$-$C_3$haloalkyl, and $C_1$-$C_3$alkyl; A represents:

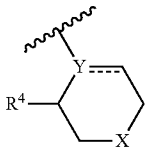

,

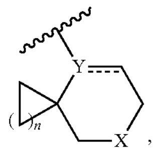

, or

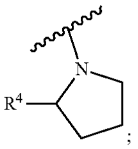

;

$\overline{- - -}$ is a single bond or a double bond; X is selected from the group consisting of $CH_2$, S, SO, $SO_2$, $NR^5$, $NCOR^5$, $NCOR^9$, $NCOCH_2R^9$, O, and a bond; Y is selected from the group consisting of N, CH, and C, provided that, when Y is CH, $\overline{- - -}$ is a single bond; n is selected from 1, 2, 3 and 4; each $R^4$ is independently selected from the group consisting of H, halogen, $COR^6$, $C_1$-$C_6$alkyl, $C_1$-$C_3$alkoxy$C_1$-$C_3$alkyl, $C_1$-$C_6$alkoxy, $C_3$-$C_6$cycloalkyl, $C_3$-$C_6$heterocyclyl, $C_1$-$C_3$cyanoalkyl, $C_1$-$C_3$haloalkyl, aryl, and heteroaryl, wherein said aryl and said heteroaryl are optionally substituted with one or more $R^7$; $R^5$ is selected from the group consisting of H, $C_1$-$C_3$fluoroalkyl, $C_1$-$C_3$alkyl, $C_1$-$C_3$alkoxy$C_1$-$C_3$alkyl, and $C_3$-$C_6$cycloalkyl; $R^6$ is selected from the group consisting of $C_1$-$C_3$alkoxy, N—$C_1$-$C_3$alkylamino, N.N-di$C_1$-$C_3$alkylamino, 1-pyrrolidinyl, 1-piperidinyl, and 1-azetidinyl; each $R^7$ is independently selected from the group consisting of $C_1$-$C_6$alkyl, $C_3$-$C_6$cycloalkyl, $C_1$-$C_3$alkoxy$C_1$-$C_3$alkyl, $C_1$-$C_3$haloalkyl, halogen, N—$C_1$-$C_3$alkylamino, N.N-di$C_1$-$C_3$alkylamino, $C_1$-$C_3$haloalkoxy and $C_1$-$C_3$alkoxy; $R^9$ is selected from the group consisting of $C_1$-$C_3$alkyl, $C_1$-$C_3$alkoxy, $C_3$-$C_6$cycloalkyl, heterocyclyl, phenyl and a monocyclic heteroaryl, wherein said heterocyclyl, said phenyl and said monocyclic heteroaryl are optionally substituted with one or two $R^8$; and each $R^8$ is independently selected from the group consisting of halogen, $C_1$-$C_3$haloalkyl and $C_1$-$C_3$alkyl.

In one embodiment, described herein is a method of inhibiting transmission of a virus, a method of inhibiting viral entry, a method of inhibiting viral replication, a method of minimizing expression of viral proteins, or a method of inhibiting virus release, comprising administering a therapeutically effective amount of a compound of Formula I or pharmaceutically acceptable salt, stereoisomer, or tautomer thereof, to a patient suffering from the virus, and/or contacting an effective amount of a compound of Formula I or pharmaceutically acceptable salt, stereoisomer, or tautomer thereof, with a virally infected cell, wherein the compound of Formula I is represented by:

Formula I

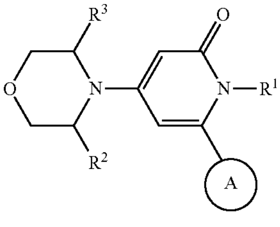

or a pharmaceutically acceptable salt, stereoisomer, or tautomer thereof, wherein: $R^1$, $R^2$, and $R^3$ are independently selected from the group consisting of H, $C_1$-$C_3$haloalkyl, and $C_1$-$C_3$alkyl; A represents:

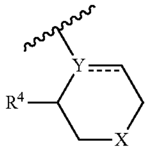 or 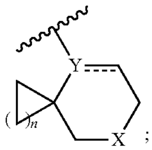 ;

$\equiv$ is a single bond or a double bond; X is selected from the group consisting of $CH_2$, S, SO, $SO_2$, $NR^5$, $NCOR^5$, $NCOR^9$, $NCOCH_2R^9$, O, and a bond; Y is selected from the group consisting of N, CH, and C, provided that, when Y is CH, $\equiv$ is a single bond; n is selected from 1, 2, 3 and 4; $R^4$ is selected from the group consisting of H, halogen, $COR^6$, $C_1$-$C_6$alkyl, $C_1$-$C_3$alkoxy$C_1$-$C_3$alkyl, $C_1$-$C_6$alkoxy, $C_3$-$C_6$cycloalkyl, $C_3$-$C_6$heterocyclyl, $C_1$-$C_3$cyanoalkyl, $C_1$-$C_3$haloalkyl, aryl, and heteroaryl, wherein said aryl and said heteroaryl are optionally substituted with one or more $R^7$; $R^5$ is selected from the group consisting of H, $C_1$-$C_3$fluoroalkyl, $C_1$-$C_3$alkyl, $C_1$-$C_3$alkoxy$C_1$-$C_3$alkyl, and $C_3$-$C_6$cycloalkyl; $R^6$ is selected from the group consisting of $C_1$-$C_3$alkoxy, N—$C_1$-$C_3$alkylamino, N.N-di$C_1$-$C_3$alkylamino, 1-pyrrolidinyl, 1-piperidinyl, and 1-azetidinyl; each $R^7$ is independently selected from the group consisting of $C_1$-$C_6$alkyl, $C_3$-$C_6$cycloalkyl, $C_1$-$C_3$alkoxy$C_1$-$C_3$alkyl, $C_1$-$C_3$haloalkyl, halogen, N—$C_1$-$C_3$alkylamino, N.N-di$C_1$-$C_3$alkylamino, $C_1$-$C_3$haloalkoxy and $C_1$-$C_3$alkoxy; $R^9$ is selected from the group consisting of $C_1$-$C_3$alkyl, $C_1$-$C_3$alkoxy, $C_3$-$C_6$cycloalkyl, heterocyclyl, phenyl and a monocyclic heteroaryl, wherein said heterocyclyl, said phenyl and said monocyclic heteroaryl are optionally substituted with one or two $R^8$; and each $R^8$ is independently selected from the group consisting of halogen, $C_1$-$C_3$haloalkyl and $C_1$-$C_3$alkyl.

In some embodiments, $R^1$ is H. In some embodiments, $R^2$ is H. In some embodiments, $R^3$ is $C_1$-$C_3$alkyl. In some embodiments, A is piperidinyl. In some embodiments, $R^4$ is $C_1$-$C_3$haloalkyl. In some embodiments, n is 2.

In some embodiments, the compound is selected from the group consisting of: 4-morpholino-6-(2-phenylpyrrolidin-1-yl)-1H-pyridin-2-one; 1-methyl-4-morpholino-6-(2-phenylpyrrolidin-1-yl)pyridin-2-one; 4-morpholino-6-[(2S)-2-phenylpyrrolidin-1-yl]-1H-pyridin-2-one; 4-morpholino-6-[(2R)-2-phenylpyrrolidin-1-yl]-1H-pyridin-2-one; 6-(3,6-dihydro-2H-pyran-4-yl)-4-(3-methyl morpholin-4-yl)-1H-pyridin-2-one; 4-(3-methylmorpholin-4-yl)-6-tetrahydropyran-4-yl-1H-pyridin-2-one; 6-[2-(3-methoxyphenyl)pyrrolidin-1-yl]-4-(3-methylmorpholin-4-yl)-1H-pyridin-2-one; 4-(3-methylmorpholin-4-yl)-6-[2-(3-pyridyl)pyrrolidin-1-yl]-1H-pyridin-2-one; 4-(3-methylmorpholin-4-yl)-6-(2-phenylpyrrolidin-1-yl)-1H-pyridin-2-one; N,N-dimethyl-1-[4-[(3R)-3-methylmorpholin-4-yl]-6-oxo-1H-pyridin-2-yl]pyrrolidine-2-carboxamide; 6-[2-(1-methoxy-1-methyl-ethyl)pyrrolidin-1-yl]-4-[(3R)-3-methylmorpholin-4-yl]-1H-pyridin-2-one; 6-(2-cyclohexylpyrrolidin-1-yl)-4-[(3R)-3-methylmorpholin-4-yl]-1H-pyridin-2-one; 6-[2-(3-fluorophenyl)pyrrolidin-1-yl]-4-[(3R)-3-methylmorpholin-4-yl]-1H-pyridin-2-one; 6-[2-(2,5-difluorophenyl)pyrrolidin-1-yl]-4-[(3R)-3-methylmorpholin-4-yl]-1H-pyridin-2-one; 4-[(3R)-3-methylmorpholin-4-yl]-6-[2-[3-(trifluoromethoxy)phenyl]pyrrolidin-1-yl]-1H-pyridin-2-one; 4-[(3R)-3-methylmorpholin-4-yl]-6-[2-[3-(trifluoromethyl)phenyl]pyrrolidin-1-yl]-1H-pyridin-2-one; 6-[2-(3-methoxyphenyl)pyrrolidin-1-yl]-4-[(3R)-3-methylmorpholin-4-yl]-1H-pyridin-2-one; 4-[(3R)-3-methylmorpholin-4-yl]-6-(2-phenylpyrrolidin-1-yl)-1H-pyridin-2-one; 4-[(3R)-3-methylmorpholin-4-yl]-6-[2-(1-methylpyrazol-4-yl)pyrrolidin-1-yl]-1H-pyridin-2-one; 6-[2-(1,5-dimethylpyrazol-3-yl)pyrrolidin-1-yl]-4-[(3R)-3-methylmorpholin-4-yl]-1H-pyridin-2-one; 6-[2-(1-ethylpyrazol-3-yl)pyrrolidin-1-yl]-4-[(3R)-3-methylmorpholin-4-yl]-1H-pyridin-2-one; 6-[2-(5-methyl-2-furyl)pyrrolidin-1-yl]-4-[(3R)-3-methylmorpholin-4-yl]-1H-pyridin-2-one; 6-[2-[3-(dimethylamino)phenyl]pyrrolidin-1-yl]-4-[(3R)-3-methylmorpholin-4-yl]-1H pyridin-2-one; 4-[(3R)-3-methylmorpholin-4-yl]-6-(3-methylmorpholin-4-yl)-1H-pyridin-2-one; 4-[(3R)-3-methylmorpholin-4-yl]-6-[2-(trifluoromethyl)-1-piperidyl]-1H-pyridin-2-one; 4-[(3R)-3-methylmorpholin-4-yl]-6-(3-phenylmorpholin-4-yl)-1H-pyridin-2-one; 4-[(3R)-3-methylmorpholin-4-yl]-6-(1-oxo-1,4-thiazinan-4-yl)-1H-pyridin-2-one; 6-(1,1-dioxo-1,4-thiazinan-4-yl)-4-[(3R)-3-methylmorpholin-4-yl]-1H-pyridin-2-one; 6-(4-acetylpiperazin-1-yl)-4-[(3R)-3-methylmorpholin-4-yl]-1H-pyridin-2-one; 4-[(3R)-3-methylmorpholin-4-yl]-6-[(2R)-2-phenyl-1-piperidyl]-1H-pyridin-2-one; 4-[(3R)-3-methylmorpholin-4-yl]-6-(4-methyl-2-phenyl-piperazin-1-yl)-1H-pyridin-2-one; 4-[(3R)-3-methylmorpholin-4-yl]-6-[3-(trifluoromethyl)morpholin-4-yl]-1H-pyridin-2-one; 6-(3-cyclopropylmorpholin-4-yl)-4-[(3R)-3-methylmorpholin-4-yl]-1H-pyridin-2-one; 4-[(3R)-3-methylmorpholin-4-yl]-6-[(2S)-2-(trifluoromethyl)pyrrolidin-1-yl]-1H-pyridin-2-one; 4-[(3R)-3-methylmorpholin-4-yl]-6-[(2R)-2-(trifluoromethyl)pyrrolidin-1-yl]-1H-pyridin-2-one; 6-[2-(3-chlorophenyl)pyrrolidin-1-yl]-4-[(3R)-3-methylmorpholin-4-yl]-1H-pyridin-2-one; 6-[2-(3-cyclopropylphenyl)pyrrolidin-1-yl]-4-[(3R)-3-methylmorpholin-4-yl]-1H-pyridin-2-one; 4-[(3R)-3-methylmorpholin-4-yl]-6-[2-(2-pyridyl)pyrrolidin-1-yl]-1H-pyridin-2-one; 4-[(3R)-3-methylmorpholin-4-yl]-6-(2-thiazol-2-ylpyrrolidin-1-yl)-1H-pyridin-2-one; 6-[2-(5-methylisoxazol-3-yl)pyrrolidin-1-yl]-4-[(3R)-3-methylmorpholin-4-yl]-1H-pyridin-2-one; 1-methyl-4-[(3R)-3-methylmorpholin-4-yl]-6-[(2R)-2-(trifluoromethyl)-1-piperidyl]pyridin-2-one; 4-[(3R)-3-methylmorpholin-4-yl]-6-(8-oxa-5-azaspiro[3.5]nonan-5-yl)-1H-pyridin-2-one; 6-[2-(3-methoxyphenyl)-1-piperidyl]-4-[(3R)-3-methylmorpholin-4-yl]-1H-pyridin-2-one; 6-[4-acetyl-2-(trifluoromethyl)piperazin-1-yl]-4-[(3R)-3-methylmorpholin-4-yl]-1H pyridin-2-one; 6-[4-(5-fluoropyridine-3-carbonyl)-2-(trifluoromethyl)piperazin-1-yl]-4-[(3R)-3-methylmorpholin-4-yl]-1H-pyridin-2-one; 6-[4-[2-(4-fluorophenyl)acetyl]-2-(trifluoromethyl)piperazin-1-yl]-4-[(3R)-3-methylmorpholin-4-yl]-1H-pyridin-2-one; 4-[(3R)-3-methylmorpholin-4-yl]-6-[4-(tetrahydrofuran-2-carbonyl)-2-(trifluoromethyl)piperazin-1-yl]-1H-pyridin-2-one; and 4-[(3R)-3-methylmorpholin-4-yl]-6-[4-methyl-2-(trifluoromethyl)piperazin-1-yl]-1H-pyridin-2-one; and pharmaceutically acceptable salts, stereoisomers, and tautomers thereof.

In some embodiments, the compound is selected from the group consisting of:

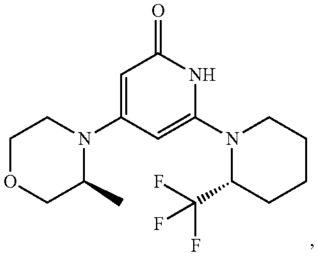

,

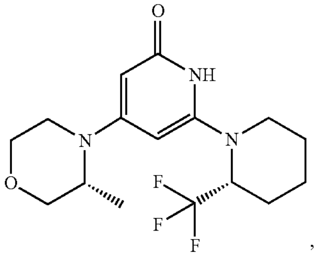

,

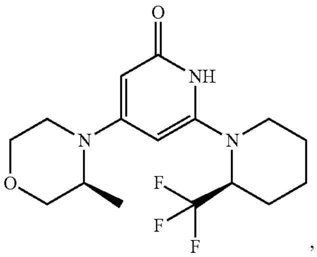

,

-continued

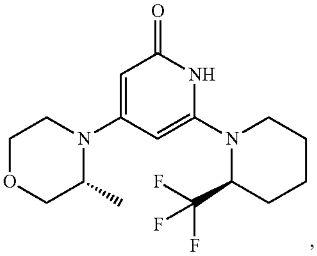

, and pharmaceutically acceptable salts, stereoisomers, and tautomers thereof.

In some embodiments, the compound is selected from the group consisting of:

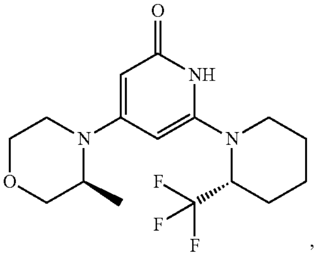

,

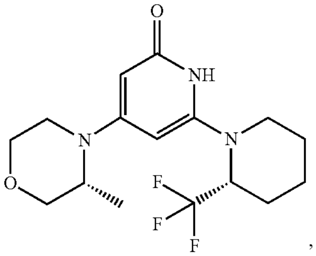

,

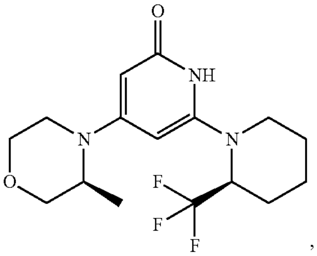

,

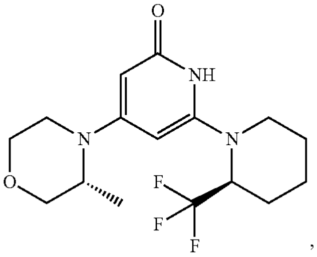

, and pharmaceutically acceptable salts thereof.

In some embodiments, the compound is selected from the group consisting of:

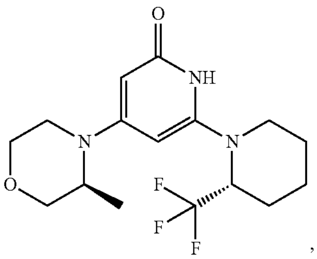

,

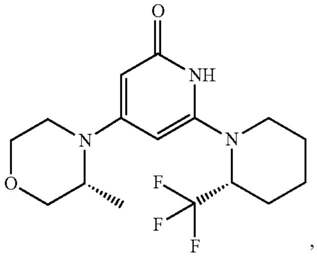

, and pharmaceutically acceptable salts thereof.

In some embodiments, the compound is selected from the group consisting of:

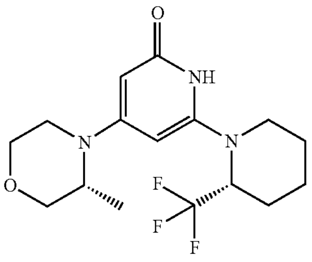

and pharmaceutically acceptable salts thereof.

In some embodiments, the viral infection is a caused by a coronavirus. In some embodiments, the viral infection is caused by a virus selected from the group consisting of a coronavirus, a rhinovirus and a flavivirus. In some embodiments, the viral infection is caused by a rhinovirus. In some embodiments, the viral infection is caused by a flavivirus.

In some embodiments, the viral infection is caused by a coronavirus selected from the group consisting of: 229E alpha coronavirus, NL63 alpha coronavirus, OC43 beta coronavirus, HKU1 beta coronavirus, Middle East Respiratory Syndrome (MERS) coronavirus (MERS-CoV), severe acute respiratory syndrome (SARS) coronavirus (SARS-CoV), and SARS-CoV-2.

In some embodiments, the viral infection is caused by SARS.

In some embodiments, the viral infection is caused by SARS-CoV.

In some embodiments, the viral infection is caused by SARS-CoV-2.

In some embodiments, the viral infection is caused by MERS-CoV.

In some embodiments, the viral infection is COVID-19.

In some embodiments, the viral infection is caused by a positive RNA virus.

In some embodiments, the virus is a positive-sense RNA virus. In some embodiments, the virus is a sense RNA virus. In some embodiments, the virus is a sense-strand RNA virus. In some embodiments, the virus a positive-strand RNA virus. In some embodiments, the virus is a positive (+) RNA virus. In some embodiments, the virus is a positive-sense single-stranded RNA virus.

In some embodiments, the positive RNA virus is selected from the group consisting of a virus of the Coronaviridae family, a virus of the Flaviviridae family, and a virus of the Picornaviridae family.

In some embodiments, the positive RNA virus is selected from the group consisting of a rhinovirus, a flavivirus, a picornavirus, and a coronavirus.

In some embodiments, the positive RNA virus is a picornavirus. In some embodiments, the positive RNA virus is a rhinovirus. In some embodiments, the positive RNA virus is a human rhinovirus. In some embodiments, the positive RNA virus is a flavivirus. In some embodiments, the positive RNA virus is coronavirus.

In some embodiments, the positive RNA virus is selected from the group consisting of SARS CoV-1, SARS CoV-2, MERS, hepatitis C (HCV), rhinovirus, Dengue virus, Zika virus, and West Nile virus.

In some embodiments, the positive RNA virus is a coronavirus.

In some embodiments, the coronavirus is selected from the group consisting of SARS CoV-1, SARS CoV-2 and MERS.

In some embodiments, the coronavirus is SARS CoV-1.

In some embodiments, the coronavirus is SARS-CoV-2.

In some embodiments, the positive RNA virus (e.g., coronavirus) is of any variant resulting from mutation or novel variants emerging from other species (e.g., species of mammals, e.g., a mink).

In some embodiments, the positive RNA virus is MERS. In some embodiments, the positive RNA virus is hepatitis C. In some embodiments, the positive RNA virus is Zika virus. In some embodiments, the positive RNA virus is Dengue virus. In some embodiments, the positive RNA virus is West Nile virus.

In some embodiments, the viral infection is a respiratory viral infection.

In some embodiments, the viral infection is an upper respiratory viral infection or a lower respiratory viral infection.

In some embodiments, the method further comprises administering a therapeutically effective amount of one or more other agents or compositions to the patient.

In some embodiments, the one or more other additional agents is selected from the group consisting of ribavirin, favipiravir, ST-193, oseltamivir, zanamivir, peramivir, danoprevir, ritonavir, and remdesivir.

In some embodiments, the one or more other additional agents is selected from the group consisting of protease inhibitors, fusion inhibitors, M2 proton channel blockers, polymerase inhibitors, 6-endonuclease inhibitors, neuraminidase inhibitors, reverse transcriptase inhibitor, aciclovir, acyclovir, protease inhibitors, arbidol, atazanavir, atripla, boceprevir, cidofovir, combivir, darunavir, docosanol, edoxudine, entry inhibitors, entecavir, famciclovir, fomivirsen, fosamprenavir, foscarnet, fosfonet, ganciclovir, ibacitabine, immunovir, idoxuridine, imiquimod, inosine, integrase inhibitor, interferons, lopinavir, loviride, moroxydine, nexavir, nucleoside analogues, penciclovir, pleconaril, podophyllotoxin, ribavirin, tipranavir, trifluridine, trizivir, tromantadine, truvada, valaciclovir, valganciclovir, vicriviroc, vidarabine, viramidine, and zodovudine.

In some embodiments, the one or more other additional agents is selected from the group consisting of lamivudine, an interferon alpha, a VAP anti-idiotypic antibody, enfuvirtide, amantadine, rimantadine, pleconaril, aciclovir, zidovudine, fomivirsen, a protease inhibitor, double-stranded RNA activated caspase oligomerizer (DRACO), rifampicin, zanamivir, oseltamivir, danoprevir, ritonavir, and remdesivir.

In some embodiments, the one or more other additional agents is selected from the group consisting of quinine (optionally in combination with clindamycin), chloroquine, amodiaquine, artemisinin and its derivatives, doxycycline, pyrimethamine, mefloquine, halofantrine, hydroxychloroquine, eflornithine, nitazoxanide, ornidazole, paromomycin, pentamidine, primaquine, pyrimethamine, proguanil (optionally in combination with atovaquone), a sulfonamide, tafenoquine, tinidazole and a PPT1 inhibitor.

In some embodiments, the one or more other additional agents is an RNA polymerase inhibitor.

In some embodiments, the RNA polymerase inhibitor is selected from the group consisting of remdesivir, sofosbuvir, 7-deaza-2-CMA, galidesvir, and AT-527.

In some embodiments, the RNA polymerase inhibitor is remdesivir.

In some embodiments, the one or more other additional agents is selected from the group consisting of a TMPRSS protease inhibitor, a lysosomal blocking agent (e.g., hydroxychloroquine), a PIKfyve inhibitor (e.g., apilimod), an anti-SARSCOV-2 antibody, a cocktail of anti-SARS-COV-2 antibodies, an anti-inflammatory agent, an anti-TNF agent (e.g., adalimumab, infliximab, etanercept, golimumab, or certolizumab), a histimine H1/H2 blocker (e.g., famotidine, nizatidine, ranitidine, and cimetidine), a steroid, an anti-coagulant, a complement targeting agent, a statin, and an ACE inhibitor.

In some embodiments, TMPRSS protease inhibitor is selected from the group consisting of a TMPRSS4 inhibitor, a TMPRSS11A inhibitor, a TMPRSS11D inhibitor, TMPRSS11E1 inhibitor, and a TMPRSS2 inhibitor.

In some embodiments, the TMPRSS protease inhibitor is a TMRSS2 protease inhibitor.

In some embodiments, the TMRESS-2 protease inhibitor is selected from camostat and nafamostat.

In some embodiments, the anti-SARSCOV-2 antibody is selected from LY-CoV555 (bamlanivimab) and LY-CoV016 (etesevimab).

In some embodiments, the cocktail of anti-SARSCOV-2 antibodies is REGN-COV2.

In some embodiments, the anti-inflammatory agent is an IL-6 antagonist (e.g., siltuximab, sarilumab, olokizumab, BMS-945429, sirukumab, and clazakizumab).

In some embodiments, the steroid is dexamethasone.

In some embodiments, the anti-coagulant is low-molecular weight heparin.

In some embodiments, the complement targeting agent is eculizumab.

In some embodiments, the statin is selected from the group consisting of atorvastatin, fluvastatin, lovastatin, pitavastatin, pravastatin, rosuvastatin, and simvastatin.

In some embodiments, the ACE inhibitor is selected from the group consisting of benazepril, captopril enalapril/enalaprilat, fosinopril, lisinopril moexipril, perindopril quinapril, and ramipril.

In some embodiments, the one or more other additional agents is selected from the group consisting of remdesivir, camostat, nafamostat, hydroxychloroquine, chloroquine, apilimod, LY-CoV555 (bamlanivimab), LY-CoV016 (etesevimab), REGN-COV2, tocilizumab, siltuximab, sarilumab, olokizumab, BMS-945429, sirukumab, clazakizumab, adalimumab, infliximab, etanercept, golimumab, certolizumab, famotidine, nizatidine, ranitidine, cimetidine, dexamethasone, low molecular weight heparin, eculizumab, atorvastatin, fluvastatin, lovastatin, pitavastatin, pravastatin, rosuvastatin, simvastatin, benazepril, captopril enalapril/enalaprilat, fosinopril, lisinopril moexipril, perindopril quinapril, and ramipril.

In some embodiments, the method comprises administering one or more one or more other additional agents selected from the group consisting of remdesivir, sofosbuvir, 7-deaza-2-CMA, galidesvir, AT-527, temoporfin, novobiocin, curcumin, voxilaprevir, grazopevir, glecaprevir, camostat, nafamostat, hydroxychloroquine, chloroquine, apilimod, imatinib, dasatinib, ponatinib, velpatasvir, ledipasvir, elbasivir, pibrentasvir, NITD008, LY-CoV555 (bamlanivimab), LY-CoV016 (etesevimab), REGN-COV2, tocilizumab, siltuximab, sarilumab, olokizumab, BMS-945429, sirukumab, clazakizumab, adalimumab, infliximab, etanercept, golimumab, certolizumab, famotidine, nizatidine, ranitidine, cimetidine, dexamethasone, low molecular weight heparin, eculizumab, atorvastatin, fluvastatin, lovastatin, pitavastatin, pravastatin, rosuvastatin, simvastatin, benazepril, captopril enalapril/enalaprilat, fosinopril, lisinopril moexipril, perindopril quinapril, ramipril, and adoptive NK cell therapy.

In some embodiments, the one or more other additional agents is selected from the group consisting of a ABL inhibitor and a JAK inhibitor.

In some embodiments, the one or more other additional agents is an ABL inhibitor (e.g., imatinib, dasatinib, or ponatinib). In some embodiments, the ABL inhibitor is selected from the group consisting of imatinib, dasatinib, and ponatinib. In some embodiments, the ABL inhibitor is imatinib. In some embodiments, the ABL inhibitor is dasatinib. In some embodiments, the ABL inhibitor is ponatinib.

In some embodiments, the one or more other additional agents is a JAK inhibitor. In some embodiments, the JAK inhibitor is selected from the group consisting of baricitinib, ruxolitinib, tofacitinib, and upadacitinib. In some embodiments, the JAK inhibitor is baricitinib. In some embodiments, the JAK inhibitor is ruxolitinib. In some embodiments, the JAK inhibitor is tofacitinib. In some embodiments, the JAK inhibitor is upadacitinib.

In some embodiments, the one or more other additional agents is a protease inhibitor. In embodiments, the protease inhibitor is selected from the group consisting of temoporfin, novobiocin, curcumin, voxilaprevir, grazopevir, and glecaprevir.

In some embodiments, the one or more other additional agents is an NS5A inhibitor. In embodiments, the NS5A inhibitor is selected from the group consisting of velpatasvir, ledipasvir, elbasivir, and pibrentasvir.

In some embodiments, the one or more other additional agents is a pyrimidine synthesis inhibitor. In some embodiments, the pyrimidine synthesis inhibitor is NITD008.

In some embodiments, the one or more other additional agents is an adoptive natural killer (NK) cell therapy.

In some embodiments, the additional therapeutic agent is a vaccine.

In some embodiments, the vaccine is a coronavirus vaccine.

In some embodiments, the vaccine is selected from the group consisting of BNT162b2, mRNA-1273, AZD1222, and Ad26.COV2.S.

In some embodiments, the vaccine is a protein-based vaccine.

In some embodiments, the vaccine is an RNA-based vaccine.

In some embodiments, the vaccine is an attenuated virus vaccine.

In some embodiments, the vaccine is an inactivated virus vaccine.

In some embodiments, the vaccine is a non-replicating viral vector vaccine.

In some embodiments, the compound is orally administered to the patient.

In some embodiments, the compound is parenterally administered to the patient.

In one embodiment, described herein is a method of treating a Coronaviridae infection in a patient in need thereof comprising administering to the patient a therapeutically effective amount of a compound represented by Formula I:

Formula I

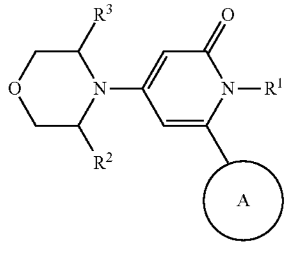

or a pharmaceutically acceptable salt, stereoisomer, or tautomer thereof, wherein: $R^1$, $R^2$, and $R^3$ are independently selected from the group consisting of H, $C_1$-$C_3$haloalkyl, and $C_1$-$C_3$alkyl; A represents:

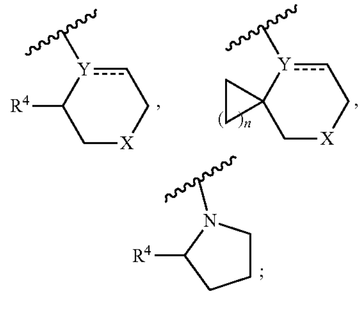

, or ;

$\overline{---}$ is a single bond or a double bond; X is selected from the group consisting of $CH_2$, S, SO, $SO_2$, $NR^5$, $NCOR^5$, $NCOR^9$, $NCOCH_2R^9$, O, and a bond; Y is selected from the group consisting of N, CH, and C, provided that, when Y is CH, $\overline{---}$ is a single bond; n is selected from 1, 2, 3 and 4; each $R^4$ is independently selected from the group consisting of H, halogen, $COR^6$, $C_1$-$C_6$alkyl, $C_1$-$C_3$alkoxy$C_1$-$C_3$alkyl, $C_1$-$C_6$alkoxy, $C_3$-$C_6$cycloalkyl, $C_3$-$C_6$heterocyclyl, $C_1$-$C_3$cyanoalkyl, $C_1$-$C_3$haloalkyl, aryl, and heteroaryl, wherein said aryl and said heteroaryl are optionally substituted with one or more $R^7$; $R^5$ is selected from the group consisting of H, $C_1$-$C_3$fluoroalkyl, $C_1$-$C_3$alkyl, $C_1$-$C_3$alkoxy$C_1$-$C_3$alkyl, and $C_3$-$C_6$cycloalkyl; $R^6$ is selected from the group consisting of $C_1$-$C_3$alkoxy, N—$C_1$-$C_3$alkylamino, N.N-di$C_1$-$C_3$alkylamino, 1-pyrrolidinyl, 1-piperidinyl, and 1-azetidinyl; each $R^7$ is independently selected from the group consisting of $C_1$-$C_6$alkyl, $C_3$-$C_6$cycloalkyl, $C_1$-$C_3$alkoxy$C_1$-$C_3$alkyl, $C_1$-$C_3$haloalkyl, halogen, N—$C_1$-$C_3$alkylamino, N.N-di$C_1$-$C_3$alkylamino, $C_1$-$C_3$haloalkoxy and $C_1$-$C_3$alkoxy; $R^9$ is selected from the group consisting of $C_1$-$C_3$alkyl, $C_1$-$C_3$alkoxy, $C_3$-$C_6$cycloalkyl, heterocyclyl, phenyl and a monocyclic heteroaryl, wherein said heterocyclyl, said phenyl and said monocyclic heteroaryl are optionally substituted with one or two $R^8$; and each $R^8$ is independently selected from the group consisting of halogen, $C_1$-$C_3$haloalkyl and $C_1$-$C_3$alkyl.

In one embodiment, described herein is a method of treating a Coronaviridae infection in a patient in need thereof comprising administering to the patient a therapeutically effective amount of a compound represented by Formula I:

Formula I

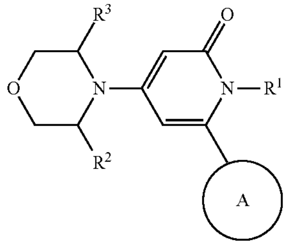

or a pharmaceutically acceptable salt, stereoisomer, or tautomer thereof, wherein: $R^1$, $R^2$, and $R^3$ are independently selected from the group consisting of H, $C_1$-$C_3$haloalkyl, and $C_1$-$C_3$alkyl; A represents:

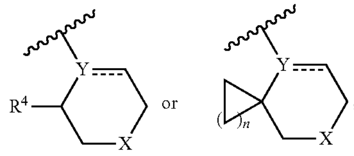

or ;

$\overline{---}$ is a single bond or a double bond; X is selected from the group consisting of $CH_2$, S, SO, $SO_2$, $NR^5$, $NCOR^5$, $NCOR^9$, $NCOCH_2R^9$, O, and a bond; Y is selected from the group consisting of N, CH, and C, provided that, when Y is CH, $\overline{---}$ is a single bond; n is selected from 1, 2, 3 and 4; $R^4$ is selected from the group consisting of H, halogen, $COR^6$, $C_1$-$C_6$alkyl, $C_1$-$C_3$alkoxy$C_1$-$C_3$alkyl, $C_1$-$C_6$alkoxy, $C_3$-$C_6$cycloalkyl, $C_3$-$C_6$heterocyclyl, $C_1$-$C_3$cyanoalkyl, $C_1$-$C_3$haloalkyl, aryl, and heteroaryl, wherein said aryl and said heteroaryl are optionally substituted with one or more $R^7$; $R^5$ is selected from the group consisting of H, $C_1$-$C_3$fluoroalkyl, $C_1$-$C_3$alkyl, $C_1$-$C_3$alkoxy$C_1$-$C_3$alkyl, and $C_3$-$C_6$cycloalkyl; $R^6$ is selected from the group consisting of $C_1$-$C_3$alkoxy, N—$C_1$-$C_3$alkylamino, N.N-di$C_1$-$C_3$alkylamino, 1-pyrrolidinyl, 1-piperidinyl, and 1-azetidinyl; each $R^7$ is independently selected from the group consisting of $C_1$-$C_6$alkyl, $C_3$-$C_6$cycloalkyl, $C_1$-$C_3$alkoxy$C_1$-$C_3$alkyl, $C_1$-$C_3$haloalkyl, halogen, N—$C_1$-$C_3$alkylamino, N.N-di$C_1$-$C_3$alkylamino, $C_1$-$C_3$haloalkoxy and $C_1$-$C_3$alkoxy; $R^9$ is selected from the group consisting of $C_1$-$C_3$alkyl, $C_1$-$C_3$alkoxy, $C_3$-$C_6$cycloalkyl, heterocyclyl, phenyl and a monocyclic heteroaryl, wherein said heterocyclyl, said phenyl and said monocyclic heteroaryl are optionally substituted with one or two $R^8$; and each $R^8$ is independently selected from the group consisting of halogen, $C_1$-$C_3$haloalkyl and $C_1$-$C_3$alkyl.

In some embodiments, $R^1$ is H. In some embodiments, $R^2$ is H. In some embodiments, $R^3$ is $C_1$-$C_3$alkyl. In some embodiments, A is piperidinyl. In some embodiments, $R^4$ is $C_1$-$C_3$haloalkyl. In some embodiments, n is 2.

In some embodiments, the compound is selected from the group consisting of: 4-morpholino-6-(2-phenylpyrrolidin-1-yl)-1H-pyridin-2-one; 1-methyl-4-morpholino-6-(2-phenylpyrrolidin-1-yl)pyridin-2-one; 4-morpholino-6-[(2S)-2-phenylpyrrolidin-1-yl]-1H-pyridin-2-one; 4-morpholino-6-[(2R)-2-phenylpyrrolidin-1-yl]-1H-pyridin-2-one; 6-(3,6-dihydro-2H-pyran-4-yl)-4-(3-methyl morpholin-4-yl)-1H-pyridin-2-one; 4-(3-methylmorpholin-4-yl)-6-tetrahydropyran-4-yl-1H-pyridin-2-one; 6-[2-(3-methoxyphenyl)pyrrolidin-1-yl]-4-(3-methylmorpholin-4-yl)-1H-pyridin-2-one; 4-(3-methylmorpholin-4-yl)-6-[2-(3-pyridyl)pyrrolidin-1-yl]-1H-pyridin-2-one; 4-(3-methylmorpholin-4-yl)-6-(2-phenylpyrrolidin-1-yl)-1H-pyridin-2-one; N,N-dimethyl-1-[4-[(3R)-3-methylmorpholin-4-yl]-6-oxo-1H-pyridin-2-yl]pyrrolidine-2-carboxamide; 6-[2-(1-methoxy-1-methyl-ethyl)pyrrolidin-1-yl]-4-[(3R)-3-methylmorpholin-4-yl]-1H-pyridin-2-one; 6-(2-cyclohexylpyrrolidin-1-yl)-4-[(3R)-3-methylmorpholin-4-yl]-1H-pyridin-2-one; 6-[2-(3-fluorophenyl)pyrrolidin-1-yl]-4-[(3R)-3-methylmorpholin-4-yl]-1H-pyridin-2-one; 6-[2-(2,5-difluorophenyl)pyrrolidin-1-yl]-4-[(3R)-3-methylmorpholin-4-yl]-1H-pyridin-2-one; 4-[(3R)-3-methylmorpholin-4-yl]-6-[2-[3-(trifluoromethoxy)phenyl]pyrrolidin-1-yl]-1H-pyridin-2-one; 4-[(3R)-3-methylmorpholin-4-yl]-6-[2-[3-(trifluoromethyl)phenyl]pyrrolidin-1-yl]-1H-pyridin-2-one; 6-[2-(3-methoxyphenyl)pyrrolidin-1-yl]-4-[(3R)-3-methylmorpholin-4-yl]-1H-pyridin-2-one; 4-[(3R)-3-methylmorpholin-4-yl]-6-(2-phenylpyrrolidin-1-yl)-1H-pyridin-2-one; 4-[(3R)-3-methylmorpholin-4-yl]-6-[2-(1-methylpyrazol-4-yl)pyrrolidin-1-yl]-1H-pyridin-2-one; 6-[2-(1,5-dimethylpyrazol-3-yl)pyrrolidin-1-yl]-4-[(3R)-3-methylmorpholin-4-yl]-1H-pyridin-2-one; 6-[2-(1-ethylpyrazol-3-yl)pyrrolidin-1-yl]-4-[(3R)-3-methylmorpholin-4-yl]-1H-pyridin-2-one; 6-[2-(5-methyl-2-furyl)pyrrolidin-1-yl]-4-[(3R)-3-methylmorpholin-4-yl]-1H-pyridin-2-one; 6-[2-[3-(dimethylamino)phenyl]pyrrolidin-1-yl]-4-[(3R)-3-methylmorpholin-4-yl]-1H pyridin-2-one; 4-[(3R)-3-methylmorpholin-4-yl]-6-(3-methylmorpholin-4-yl)-1H-pyridin-2-one; 4-[(3R)-3-methylmorpholin-4-yl]-6-[2-(trifluoromethyl)-1-piperidyl]-1H-pyridin-2-one; 4-[(3R)-3-methylmorpholin-4-yl]-6-(3-phenylmorpholin-4-yl)-1H-pyridin-2-one; 4-[(3R)-3-methylmorpholin-4-yl]-6-(1-oxo-1,4-thiazinan-4-yl)-1H-pyridin-2-one; 6-(1,1-dioxo-1,4-thiazinan-4-yl)-4-[(3R)-3-methylmorpholin-4-yl]-1H-pyridin-2-one; 6-(4-acetylpiperazin-1-yl)-4-[(3R)-3-methylmorpholin-4-yl]-1H-pyridin-2-one; 4-[(3R)-3-methylmorpholin-4-yl]-6-[(2R)-2-phenyl-1-piperidyl]-1H-pyridin-2-one; 4-[(3R)-3-methylmorpholin-4-yl]-6-(4-methyl-2-phenyl-piperazin-1-yl)-1H-pyridin-2-one; 4-[(3R)-3-methylmorpholin-4-yl]-6-[3-(trifluoromethyl)morpholin-4-yl]-1H-pyridin-2-one; 6-(3-cyclopropylmorpholin-4-yl)-4-[(3R)-3-methylmorpholin-4-yl]-1H-pyridin-2-one; 4-[(3R)-3-methylmorpholin-4-yl]-6-[(2S)-2-(trifluoromethyl)pyrrolidin-1-yl]-1H-pyridin-2-one; 4-[(3R)-3-methylmorpholin-4-yl]-6-[(2R)-2-(trifluoromethyl)pyrrolidin-1-yl]-1H-pyridin-2-one; 6-[2-(3-chlorophenyl)pyrrolidin-1-yl]-4-[(3R)-3-methylmorpholin-4-yl]-1H-pyridin-2-one; 6-[2-(3-cyclopropylphenyl)pyrrolidin-1-yl]-4-[(3R)-3-methylmorpholin-4-yl]-1H-pyridin-2-one; 4-[(3R)-3-methylmorpholin-4-yl]-6-[2-(2-pyridyl)pyrrolidin-1-yl]-1H-pyridin-2-one; 4-[(3R)-3-methylmorpholin-4-yl]-6-(2-thiazol-2-ylpyrrolidin-1-yl)-1H-pyridin-2-one; 6-[2-(5-methylisoxazol-3-yl)pyrrolidin-1-yl]-4-[(3R)-3-methylmorpholin-4-yl]-1H-pyridin-2-one; 1-methyl-4-[(3R)-3-methylmorpholin-4-yl]-6-[(2R)-2-(trifluoromethyl)-1-piperidyl]pyridin-2-one; 4-[(3R)-3-methylmorpholin-4-yl]-6-(8-oxa-5-azaspiro[3.5]nonan-5-yl)-1H-pyridin-2-one; 6-[2-(3-methoxyphenyl)-1-piperidyl]-4-[(3R)-3-methylmorpholin-4-yl]-1H-pyridin-2-one; 6-[4-acetyl-2-(trifluoromethyl)piperazin-1-yl]-4-[(3R)-3-methylmorpholin-4-yl]-1H pyridin-2-one; 6-[4-(5-fluoropyridine-3-carbonyl)-2-(trifluoromethyl)piperazin-1-yl]-4-[(3R)-3-methylmorpholin-4-yl]-1H-pyridin-2-one; 6-[4-[2-(4-fluorophenyl)acetyl]-2-(trifluoromethyl)piperazin-1-yl]-4-[(3R)-3-methylmorpholin-4-yl]-1H-pyridin-2-one; 4-[(3R)-3-methylmorpholin-4-yl]-6-[4-(tetrahydrofuran-2-carbonyl)-2-(trifluoromethyl)piperazin-1-yl]-1H-pyridin-2-one; and 4-[(3R)-3-methylmorpholin-4-yl]-6-[4-methyl-2-(trifluoromethyl)piperazin-1-yl]-1H-pyridin-2-one; and pharmaceutically acceptable salts, stereoisomers, and tautomers thereof.

In some embodiments, $R^1$ is H. In some embodiments, $R^2$ is H. In some embodiments, $R^3$ is $C_1$-$C_3$alkyl. In some embodiments, A is piperidinyl. In some embodiments, $R^4$ is $C_1$-$C_3$haloalkyl.

In some embodiments, the compound is selected from the group consisting of:

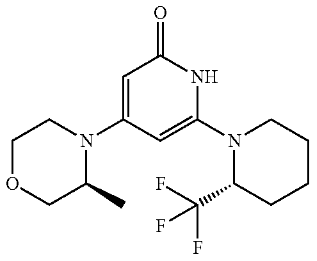
,

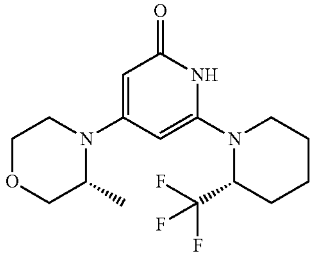
,

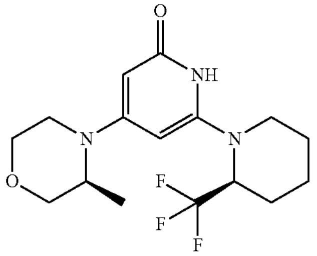
,

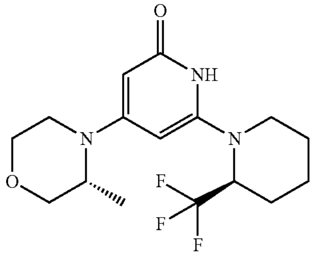
, and pharmaceutically acceptable salts, stereoisomers, and tautomers thereof.

In some embodiments, the compound is selected from the group consisting of:

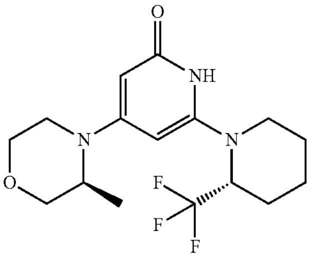
,

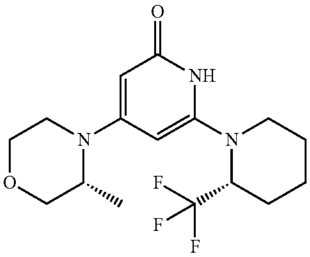 [SMILES: C[C@@H]1COCCN1c1cc(N2CCCC[C@@H]2C(F)(F)F)[nH]c(=O)c1]
,

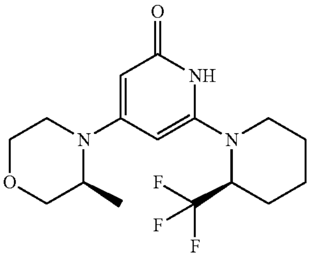
,

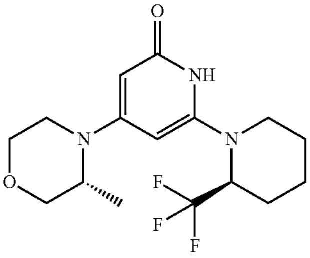
, and pharmaceutically acceptable salts thereof.

In some embodiments, the compound is selected from the group consisting of:

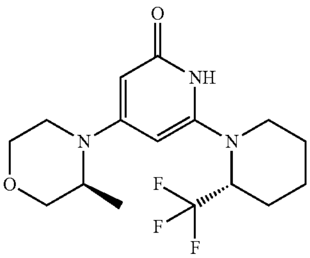
,

-continued

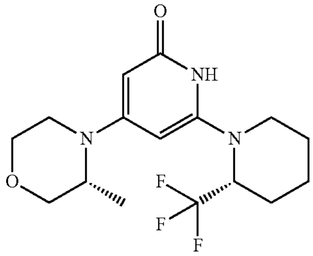
, and pharmaceutically acceptable salts thereof.

In some embodiments, the compound is selected from the group consisting of:

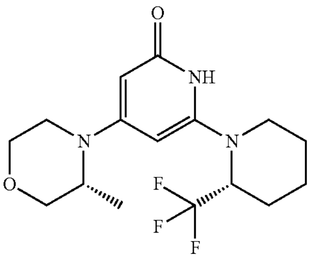

and pharmaceutically acceptable salts thereof.

In some embodiments, the Coronaviridae infection is caused by SARS-CoV-2.

In some embodiments, the Coronaviridae infection is COVID-19.

In some embodiments, the Coronaviridae infection is caused by a coronavirus.

In some embodiments, the coronavirus is selected from the group consisting of: 229E alpha coronavirus, NL63 alpha coronavirus, OC43 beta coronavirus, HKU1 beta coronavirus, Middle East Respiratory Syndrome (MERS) coronavirus (MERS-CoV), severe acute respiratory syndrome (SARS) coronavirus (SARS-CoV), and SARS-CoV-2.

In some embodiments, the coronavirus is SARS-CoV-2.

In some embodiments, the method further comprises administering a therapeutically effective amount of one or more other agents or compositions to the patient.

In some embodiments, the one or more other additional agents is selected from the group consisting of ribavirin, favipiravir, ST-193, oseltamivir, zanamivir, peramivir, danoprevir, ritonavir, and remdesivir.

In some embodiments, the one or more other additional agents is selected from the group consisting of protease inhibitors, fusion inhibitors, M2 proton channel blockers, polymerase inhibitors, 6-endonuclease inhibitors, neuraminidase inhibitors, reverse transcriptase inhibitor, aciclovir, acyclovir, protease inhibitors, arbidol, atazanavir, atripla, boceprevir, cidofovir, combivir, darunavir, docosanol, edoxudine, entry inhibitors, entecavir, famciclovir, fomivirsen, fosamprenavir, foscarnet, fosfonet, ganciclovir, ibacitabine, immunovir, idoxuridine, imiquimod, inosine, integrase inhibitor, interferons, lopinavir, loviride, moroxydine, nexavir, nucleoside analogues, penciclovir, pleconaril, podophyllotoxin, ribavirin, tipranavir, trifluridine, trizivir, tromantadine, truvada, valaciclovir, valganciclovir, vicriviroc, vidarabine, viramidine, and zodovudine.

In some embodiments, the one or more other additional agents is selected from the group consisting of lamivudine, an interferon alpha, a VAP anti-idiotypic antibody, enfuvirtide, amantadine, rimantadine, pleconaril, aciclovir, zidovudine, fomivirsen, a protease inhibitor, double-stranded RNA activated caspase oligomerizer (DRACO), rifampicin, zanamivir, oseltamivir, danoprevir, ritonavir, and remdesivir.

In some embodiments, the one or more other additional agents is selected from the group consisting of quinine (optionally in combination with clindamycin), chloroquine, amodiaquine, artemisinin and its derivatives, doxycycline, pyrimethamine, mefloquine, halofantrine, hydroxychloroquine, eflornithine, nitazoxanide, ornidazole, paromomycin, pentamidine, primaquine, pyrimethamine, proguanil (optionally in combination with atovaquone), a sulfonamide, tafenoquine, tinidazole and a PPT1 inhibitor.

In some embodiments, the one or more other additional agents is an RNA polymerase inhibitor.

In some embodiments, the RNA polymerase inhibitor is selected from the group consisting of remdesivir, sofosbuvir, 7-deaza-2-CMA, galidesvir, and AT-527.

In some embodiments, the RNA polymerase inhibitor is remdesivir.

In some embodiments, the one or more other additional agents is selected from the group consisting of a TMPRSS protease inhibitor, a lyosomal blocking agent (e.g., hydroxychloroquine), a PIKfyve inhibitor (e.g., apilimod), an anti-SARSCOV-2 antibody, a cocktail of anti-SARSCOV-2 antibodies, an anti-inflammatory agent, an anti-TNF agent (e.g., adalimumab, infliximab, etanercept, golimumab, or certolizumab), a histimine H1/H2 blocker (e.g., famotidine, nizatidine, ranitidine, and cimetidine), a steroid, an anti-coagulant, a complement targeting agent, a statin, and an ACE inhibitor.

In some embodiments, TMPRSS protease inhibitor is selected from the group consisting of a TMPRSS4 inhibitor, a TMPRSS11A inhibitor, a TMPRSS11D inhibitor, TMPRSS11E1 inhibitor, and a TMPRSS2 inhibitor.

In some embodiments, the TMPRSS protease inhibitor is a TMRSS2 protease inhibitor.

In some embodiments, the TMRESS-2 protease inhibitor is selected from camostat and nafamostat.

In some embodiments, the anti-SARS CoV-2 antibody is selected from LY-CoV555 (bamlanivimab) and LY-CoV016 (etesevimab).

In some embodiments, the cocktail of anti-SARS CoV-2 antibodies is REGN-COV2.

In some embodiments, the anti-inflammatory agent is an IL-6 antagonist (e.g., siltuximab, sarilumab, olokizumab, BMS-945429, sirukumab, and clazakizumab).

In some embodiments, the steroid is dexamethasone.

In some embodiments, the anti-coagulant is low-molecular weight heparin.

In some embodiments, the complement targeting agent is eculizumab.

In some embodiments, the statin is selected from the group consisting of atorvastatin, fluvastatin, lovastatin, pitavastatin, pravastatin, rosuvastatin, and simvastatin.

In some embodiments, the ACE inhibitor is selected from the group consisting of benazepril, captopril enalapril/enalaprilat, fosinopril, lisinopril moexipril, perindopril quinapril, and ramipril.

In some embodiments, the one or more other additional agents is selected from the group consisting of remdesivir, camostat, nafamostat, hydroxychloroquine, chloroquine, apilimod, LY-CoV555 (bamlanivimab), LY-CoV016 (etesevimab), REGN-COV2, tocilizumab, siltuximab, sarilumab, olokizumab, BMS-945429, sirukumab, clazakizumab, adalimumab, infliximab, etanercept, golimumab, certolizumab, famotidine, nizatidine, ranitidine, cimetidine, dexamethasone, low molecular weight heparin, eculizumab, atorvastatin, fluvastatin, lovastatin, pitavastatin, pravastatin, rosuvastatin, simvastatin, benazepril, captopril enalapril/enalaprilat, fosinopril, lisinopril moexipril, perindopril quinapril, and ramipril.

In some embodiments, the method comprises administering one or more one or more other additional agents selected from the group consisting of remdesivir, sofosbuvir, 7-deaza-2-CMA, galidesvir, AT-527, temoporfin, novobiocin, curcumin, voxilaprevir, grazopevir, glecaprevir, camostat, nafamostat, hydroxychloroquine, chloroquine, apilimod, imatinib, dasatinib, ponatinib, velpatasvir, ledipasvir, elbasivir, pibrentasvir, NITD008, LY-CoV555 (bamlanivimab), LY-CoV016 (etesevimab), REGN-COV2, tocilizumab, siltuximab, sarilumab, olokizumab, BMS-945429, sirukumab, clazakizumab, adalimumab, infliximab, etanercept, golimumab, certolizumab, famotidine, nizatidine, ranitidine, cimetidine, dexamethasone, low molecular weight heparin, eculizumab, atorvastatin, fluvastatin, lovastatin, pitavastatin, pravastatin, rosuvastatin, simvastatin, benazepril, captopril enalapril/enalaprilat, fosinopril, lisinopril moexipril, perindopril quinapril, ramipril, and adoptive NK cell therapy.

In some embodiments, the one or more other additional agents is an ABL inhibitor (e.g., imatinib, dasatinib, or ponatinib).

In some embodiments, the one or more other additional agents is a protease inhibitor. In embodiments, the protease inhibitor is selected from the group consisting of temoporfin, novobiocin, curcumin, voxilaprevir, grazopevir, and glecaprevir.

In some embodiments, the one or more other additional agents is an NS5A inhibitor. In embodiments, the NS5A inhibitor is selected from the group consisting of velpatasvir, ledipasvir, elbasivir, and pibrentasvir.

In some embodiments, the one or more other additional agents is a pyrimidine synthesis inhibitor. In some embodiments, the pyrimidine synthesis inhibitor is NITD008.

In some embodiments, the one or more other additional agents is an adoptive natural killer (NK) cell therapy.

In some embodiments, the additional therapeutic agent is a vaccine.

In some embodiments, the vaccine is a coronavirus vaccine.

In some embodiments, the vaccine is selected from the group consisting of BNT162b2, mRNA-1273, AZD1222, and Ad26.COV2.S.

In some embodiments, the vaccine is a protein-based vaccine.

In some embodiments, the vaccine is an RNA-based vaccine.

In some embodiments, the vaccine is an attenuated virus vaccine.

In some embodiments, the vaccine is an inactivated virus vaccine.

In some embodiments, the vaccine is a non-replicating viral vector vaccine.

In some embodiments, the compound is orally administered to the patient.

In some embodiments, the compound is parenterally administered to the patient.

In some embodiments, a Coronaviridae infection described herein is caused by a coronavirus. In some embodiments, a Coronaviridae infection described herein is caused by SARS-CoV-2. In some embodiments, a Coronaviridae infection described herein is COVID-19. In some embodiments, the coronavirus is selected from the group consisting of: 229E alpha coronavirus, NL63 alpha coronavirus, OC43 beta coronavirus, HKU1 beta coronavirus, Middle East Respiratory Syndrome (MERS) coronavirus (MERS-CoV), severe acute respiratory syndrome (SARS) coronavirus (SARS-CoV). In some embodiments, the coronavirus is SARS-CoV-2.

In some embodiments, a method described herein prevents morbidity or mortality of the patient. In some embodiments, a method described herein minimizes or prevents a need to hospitalize the patient. or minimizes or prevents a need to connect a ventilation unit to the patient. In some embodiments, a method described herein minimizes or prevents a need to hospitalize the patient in an Intensive Care Unit. In some embodiments, a method described herein minimizes or prevents a need to connect a ventilation unit to the patient.

Methods for determination of anti-viral activity for SARS CoV-1, SARS CoV-2, MERS, hepatitis C, Dengue virus, or Zika virus are known to those skilled in the art and include cytopathic effect assays (CPE), RT/PCR assays, replicon assays with a reporter readout, or viral plaque assays.

Methods for determination of inhibition of autophagosome formation in virally infected cells are known to those skilled in the art and include puncta determination by Cyto-ID® or by electron microscopy, autophagic flux assays including LC3-luciferase fusion assay or LC3-GFP/mCherry flux assay, or determination of the ratios of LC3-I/LC3-II. Such autophagy assays can also be used to evaluate the activation of autophagy by nonstructural protein 6 (nsp6) or related +RNA virus encoded proteins.

Combination Therapy

Compounds described herein, e.g., a compound of Formula I as defined herein, can be administered in combination with one or more additional therapeutic agents (e.g., one or more other additional agents described herein) to treat a disorder described herein, such as an infection by a virus described herein, e.g., a coronavirus. For example, provided in the present disclosure is a pharmaceutical composition comprising a compound described herein, e.g., a compound of Formula I as defined herein, one or more additional therapeutic agents, and a pharmaceutically acceptable excipient. In some embodiments, a compound of Formula I as defined herein and one additional therapeutic agent is administered. In some embodiments, a compound of Formula I as defined herein and two additional therapeutic agents are administered. In some embodiments, a compound of Formula I as defined herein and three additional therapeutic agents are administered. Combination therapy can be achieved by administering two or more therapeutic agents, each of which is formulated and administered separately. For example, a compound of Formula I as defined herein and an additional therapeutic agent can be formulated and administered separately. Combination therapy can also be achieved by administering two or more therapeutic agents in a single formulation, for example a pharmaceutical composition comprising a compound of Formula I as one therapeutic agent and one or more additional therapeutic agents such as an antibiotic, a viral protease inhibitor, or an anti-viral nucleoside anti-metabolite. For example, a compound of Formula I as defined herein and an additional therapeutic agent can be administered in a single formulation. Other combinations are also encompassed by combination therapy. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or weeks of each other. In some cases, even longer intervals are possible. While in many cases it is desirable that the two or more agents used in a combination therapy be present in within the patient's body at the same time, this need not be so.

Combination therapy can also include two or more administrations of one or more of the agents used in the combination using different sequencing of the component agents. For example, if agent X and agent Y are used in a combination, one could administer them sequentially in any combination one or more times, e.g., in the order X-Y-X, X-X-Y, Y-X-Y, Y-Y-X, X-X-Y-Y, etc.

Pharmaceutical Compositions and Kits

Another aspect of this disclosure provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions may be used in the form of a pharmaceutical preparation, for example, in solid, semisolid or liquid form, which contains one or more of the compounds described herein, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound provided herein, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof, and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous, or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present disclosure may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of the present disclosure suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions provided herein include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants.

In another aspect, provided are enteral pharmaceutical formulations including a disclosed compound and an enteric material, and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5.

Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives described herein.

Advantageously, provided herein are kits for use by a e.g., a consumer in need of treatment of a disease or disorder described herein, such as an infection caused by a pathogen described herein, e.g., a virus, fungus, or protozoan. Such kits include a suitable dosage form such as those described above and instructions describing the method of using such dosage form to mediate, reduce or prevent inflammation. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

EXAMPLES

The compounds described herein can be prepared in a number of ways based on the teachings contained herein and disclosures of synthetic procedures in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

Abbreviations: MS: mass spectrometry; NMR: nuclear magnetic resonance.

Example 1. Exemplary Synthesis of Compounds 1, 2, 3, 4, and 5

Compounds 1, 2, 3, 4, and 5 were prepared according to synthetic procedures described in WO 2017/140843.

For Compound 3: $^{1}$H NMR (500 MHz, DMSO-d6) δ ppm 1.07 (d, J=6.62 Hz, 3H) 1.95-2.12 (m, 4H) 2.99 (td, J=12.30, 3.78 Hz, 1H) 3.24-3.32 (m, 2H) 3.46 (td, J=11.74, 2.68 Hz, 1H) 3.55-3.65 (m, 2H) 3.65-3.73 (m, 1H) 3.89 (m, J=7.90 Hz, 2H) 4.98 (m, J=7.30, 7.30 Hz, 1H) 5.33 (s, 1H) 5.44 (s, 1H) 9.75 (br s, 1H); MS m/z 332 $[M+H]^+$.

Example 2. Compound 1 Exhibits Antiviral Activity in a SARS CoV-1 CPE Assay

A cell-based assay was used to measure the cytopathic effect (CPE) of the virus infecting Vero E6 host cells. Host cells infected with virus die as a consequence of the virus hijacking the cellular mechanisms for genome replication. The CPE reduction assay indirectly monitors the effect of antiviral agents acting through various molecular mechanisms by measuring the viability of host cells three days after inoculation with virus. Anti-viral compounds are identified as those that protect the host cells from the cytopathic effect of the virus, thereby increasing viability.

Vero E6 cells selected for expression of the SARS CoV receptor (ACE2; angiotensin-converting enzyme 2) were used for the CPE assay. Cells were grown in MEM/10% HI FBS supplemented and harvested in MEM/1% PSG/supplemented 2% HI FBS. Cells were batch inoculated with coronavirus (Toronto 2 SARS CoV-1, at M.O.I.~0.002 which resulted in 5% cell viability 72 hours post infection. Assay Ready Plates (ARPs; Corning 3712BC) pre-drugged with test compound (30-90 nL sample in 100% DMSO per well dispensed using a Labcyte ECHO 550) were prepared in the BSL-2 lab by adding 5 μL assay media to each well. The plates were passed into the BSL-3 facility where a 25 μL aliquot of virus inoculated cells (4000 Vero E6 cells/well)

was added to each well in columns 3-22. The wells in columns 23-24 contained virus infected cells only (no compound treatment). Prior to virus infection, a 25 μL aliquot of cells was added to columns 1-2 of each plate for the cell only (no virus) controls. After incubating plates at 37° C./5% $CO_2$ and 90% humidity for 72 hours, 30 μL of Cell Titer-Glo (Promega) was added to each well. Luminescence was read using a Perkin Elmer Envision or BMG CLARIOstar plate reader following incubation at room temperature for 10 minutes to measure cell viability. Raw data from each test well was normalized to the average signal of non-infected cells (Avg Cells; 100% inhibition) and virus infected cells only (Avg Virus; 0% inhibition) to calculate % inhibition of CPE using the following formula: % inhibition=100*(Test Cmpd−Avg Virus)/(Avg Cells−Avg Virus). The SARS CPE assay was conducted in BSL-3 containment with plates being sealed with a clear cover and surface decontaminated prior to luminescence reading.

Figure 2:
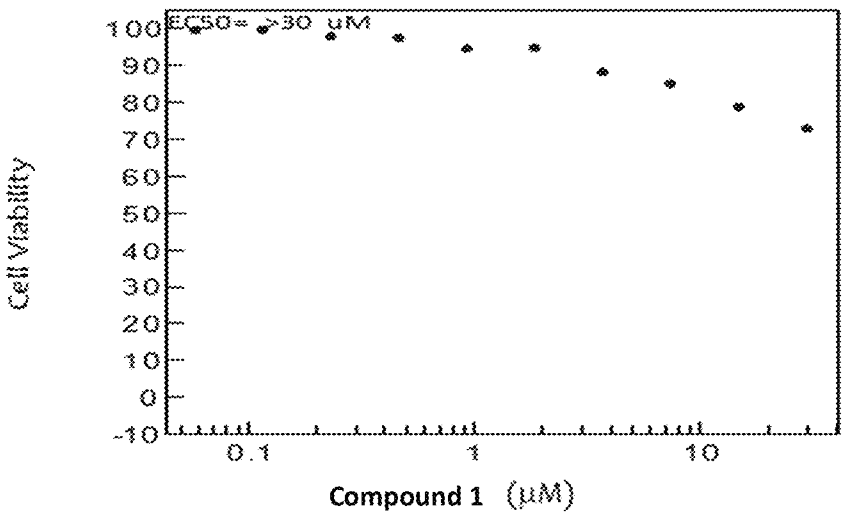
FIG. 2 depicts exemplary cell viability of Vero E6 cells with respect to Compound 1 dosing.

Compound 1 was tested in a 10-point dose response (high concentration 15 μM→two-fold dilution), affording an $IC_{50}$ of 650 nM for inhibition of SARS CoV-1 mediated cell killing (FIG. 1). Compound 1 did not exhibit general cytotoxic effects, affording a CC50>30 μM (FIG. 2).

Compound cytotoxicity (CC50) was assessed in a BSL-2 counter screen as follows: Host cells in media were added in 25 μl aliquots (4000 cells/well) to each well of assay ready plates prepared with test compounds as above. Cells only (100% viability) and cells treated with hyamine at 100 μM final concentration (0% viability) served as the high and low signal controls, respectively, for cytotoxic effect in the assay. DMSO was maintained at a constant concentration for all wells (0.3%) as dictated by the dilution factor of stock test compound concentrations. After incubating plates at 37° C./5% $CO_2$ and 90% humidity for 72 hours, 30 μl Cell Titer-Glo (Promega) was added to each well. Luminescence was read using a BMG PHERAstar plate reader following incubation at room temperature for 10 minutes to measure cell viability. Compound 1 did not exhibit general cytotoxic effects in Vero E6 cells, affording a CC50>30 μM (FIG. 2).

Figure 3:
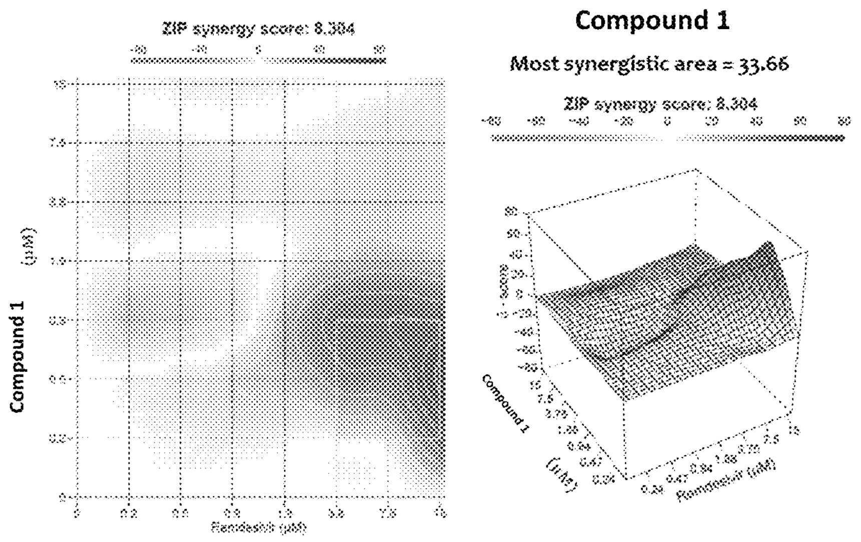
FIG. 3 depicts exemplary synergy analysis of Compound 1 and remdesivir in a SARS CoV-1 cytopathic effect (CPE) assay.

Example 3. Compound 1 Exhibits Synergy in Combination with Remdesivir in a SARS CoV-1 CPE Assay Using the assay protocol from Example 2, one or more other additional agents was tested in combination with remdesivir. Each agent was evaluated in a 10-point dose response (high concentration 15 μM→two-fold dilution). The combination treatment exhibited synergy, with a maximum ZIP synergy score of 33.66 and an average plate ZIP synergy score of 8.304 (FIG. 3). Synergy with Compound 1 was realized at concentrations up to ~1.9 μM whereas concentrations of Compound 1 above ~1.9 mM did not afford synergy due to essentially complete inhibited viral cytopathic effect as a single agent. Remdesivir synergy was realized at concentrations above ~1.9 μM.

Figure 4:
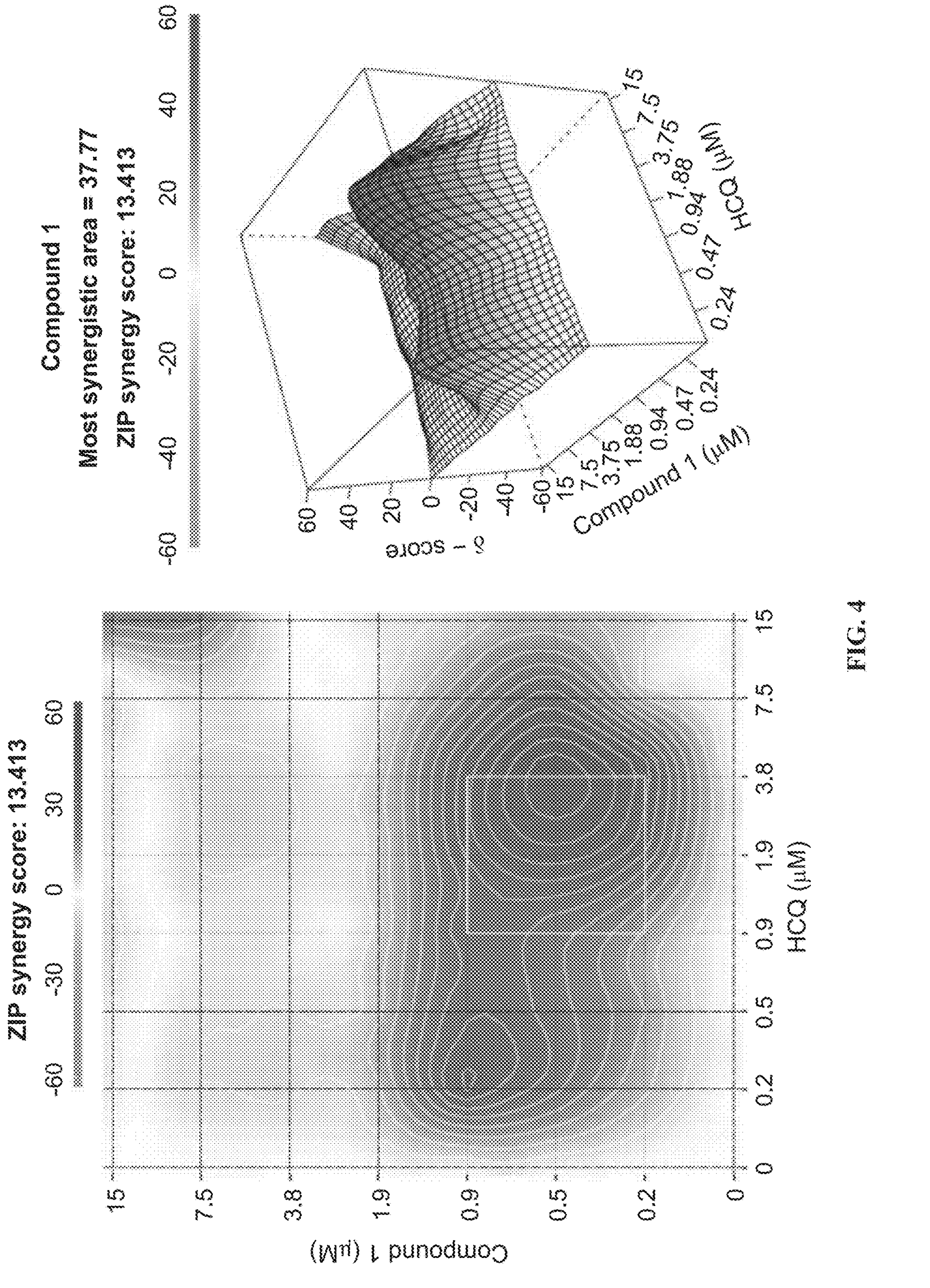
FIG. 4 depicts exemplary synergy analysis of Compound 1 and hydroxychloroquine in a SARS CoV-1 cytopathic effect (CPE) assay.

Example 4. Compound 1 Exhibits Synergy in Combination with Hydroxychloroquine in a SARS CoV-1 CPE Assay Using the assay protocol from Example 2, one or more other additional agents was tested in combination with hydroxychloroquine (HCQ). Each agent was evaluated in a 10-point dose response (high concentration 15 μM→two-fold dilution). The combination treatment exhibited synergy, with a maximum ZIP synergy score of 37.77 and an average plate ZIP synergy score of 13.413 (FIG. 4). Synergy with Compound 1 was realized at concentrations up to ~1.9 μM whereas concentrations of Compound 1 above 1.9 μM did not afford synergy due to essentially complete inhibited viral cytopathic effect as a single agent. HCQ synergy was realized at concentrations above ~0.1 μM.

Example 5. Compounds 1, 2, 3, 4, and 5 Exhibit Antiviral Activity in a SARS CoV-2 CPE Assay A cell-based assay was used to measure the cytopathic effect (CPE) of the virus infecting Vero E6 host cells. Host cells infected with virus die as a consequence of the virus hijacking the cellular mechanisms for genome replication. The CPE reduction assay indirectly monitors the effect of antiviral agents acting through various molecular mechanisms by measuring the viability of host cells three days after inoculation with virus. Anti-viral compounds are identified as those that protect the host cells from the cytopathic effect of the virus, thereby increasing viability.

Vero E6 cells selected for expression of the SARS CoV receptor (ACE2; angiotensin-converting enzyme 2) were used for the CPE assay. Cells were grown in MEM/10% HI FBS supplemented and harvested in MEM/1% PSG/supplemented 2% HI FBS. Cells were batch inoculated with coronavirus USA_WA1/2020 SARS CoV-2, at M.O.I.~0.002 which resulted in 5% cell viability 72 hours post infection. Assay Ready Plates (ARPs; Corning 3712BC) pre-drugged with test compound (30-90 nL sample in 100% DMSO per well dispensed using a Labcyte ECHO 550) were prepared in the BSL-2 lab by adding 5 μL assay media to each well. The plates were passed into the BSL-3 facility where a 25 μL aliquot of virus inoculated cells (4000 Vero E6 cells/well) was added to each well in columns 3-22. The wells in columns 23-24 contained virus infected cells only (no compound treatment). Prior to virus infection, a 25 μL aliquot of cells was added to columns 1-2 of each plate for the cell only (no virus) controls. After incubating plates at 37° C./5% $CO_2$ and 90% humidity for 72 hours, 30 μL of Cell Titer-Glo (Promega) was added to each well. Luminescence was read using a Perkin Elmer Envision or BMG CLARIOstar plate reader following incubation at room temperature for 10 minutes to measure cell viability. Raw data from each test well was normalized to the average signal of non-infected cells (Avg Cells; 100% inhibition) and virus infected cells only (Avg Virus; 0% inhibition) to calculate % inhibition of CPE using the following formula: % inhibition=100*(Test Cmpd−Avg Virus)/(Avg Cells−Avg Virus). The SARS CPE assay was conducted in BSL-3 containment with plates being sealed with a clear cover and surface decontaminated prior to luminescence reading.

Figure 5:
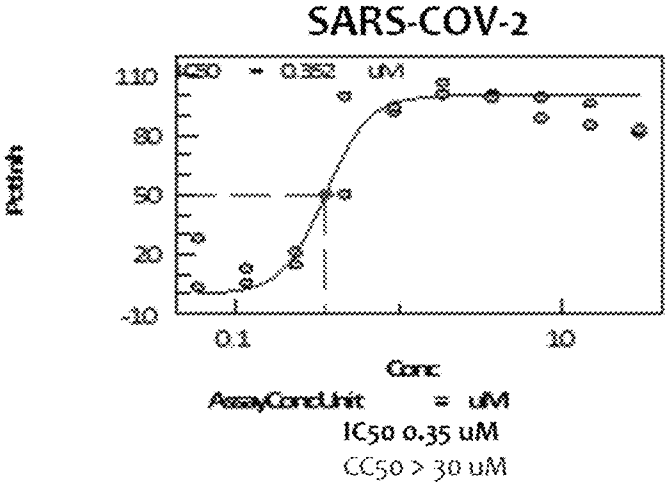
FIG. 5 depicts exemplary dose response of Compound 1 for inhibition of SARS CoV-2 mediated cell killing.

Compound 1 was tested in a 10-point dose response (high concentration 15 μM→two-fold dilution), affording an $IC_{50}$ of 350 nM for inhibition of SARS CoV-2 mediated cell killing (FIG. 5). Compound 1 did not exhibit general cytotoxic effects, affording a CC50>30 μM.

Compound 2 was tested in a 10-point dose response (high concentration 15 μM→two-fold dilution), affording an $IC_{50}$ of 4,370 nM for inhibition of SARS CoV-2 mediated cell killing. Compound 2 did not exhibit general cytotoxic effects in Vero E6 cells, affording a CC50>30 μM.

Compound 3 was tested in a 10-point dose response (high concentration 15 μM→two-fold dilution), affording an $IC_{50}$ of 2,010 nM for inhibition of SARS CoV-2 mediated cell killing. Compound 3 did not exhibit general cytotoxic effects in Vero E6 cells, affording a CC50>30 μM.

Compound 4 was tested in a 10-point dose response (high concentration 15 μM→two-fold dilution), affording an $IC_{50}$ of 1,400 nM for inhibition of SARS CoV-2 mediated cell killing. Compound 4 did not exhibit general cytotoxic effects in Vero E6 cells, affording a CC50>30 μM.

Compound 5 was tested in a 10-point dose response (high concentration 15 μM→two-fold dilution), affording an $IC_{50}$ of >10 μM for inhibition of SARS CoV-2 mediated cell killing. Compound 5 did not exhibit general cytotoxic effects in Vero E6 cells, affording a CC50>10 μM.

Figure 6:
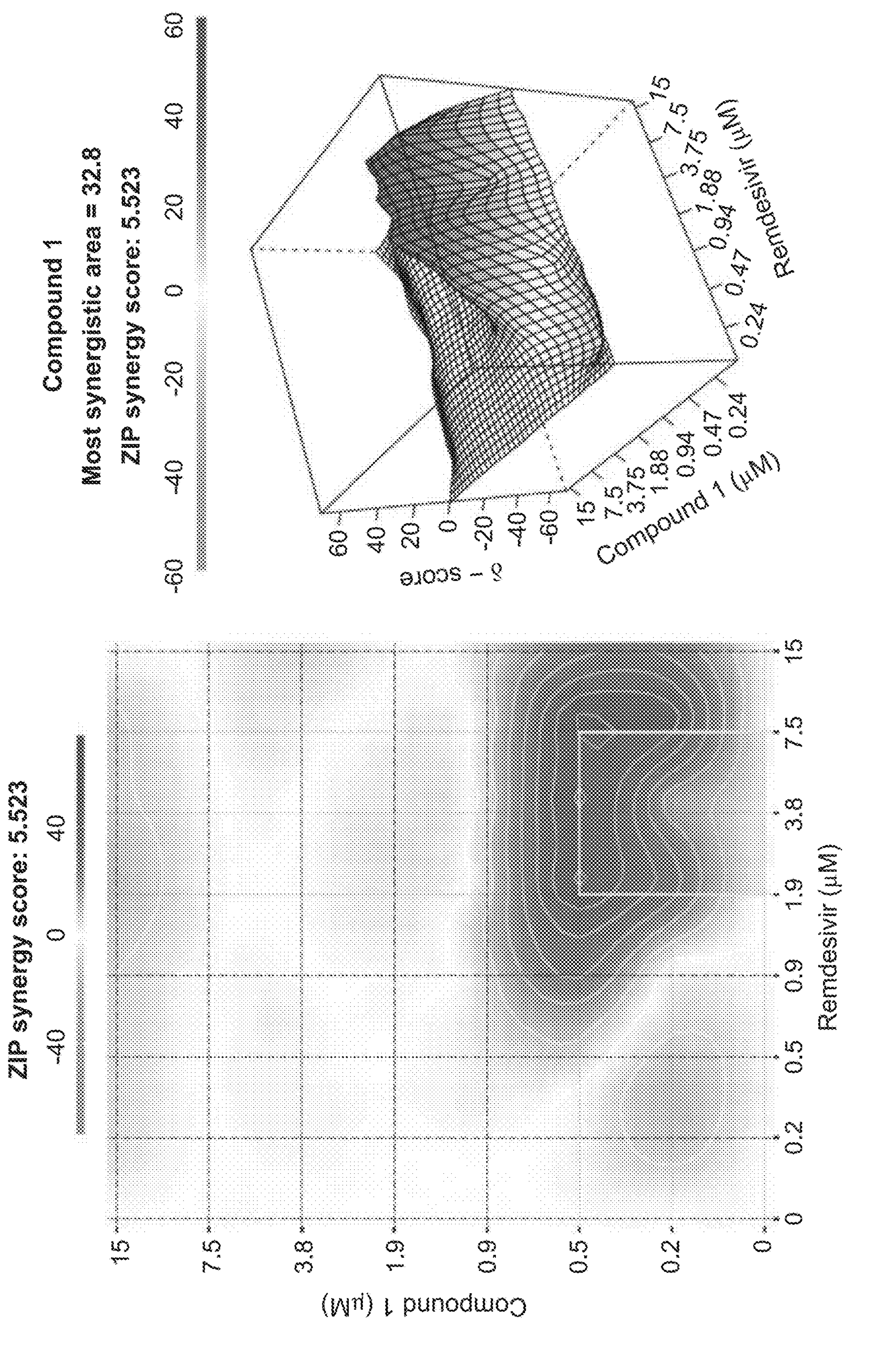
FIG. 6 depicts exemplary synergy analysis of Compound 1 and remdesivir in a SARS CoV-2 cytopathic effect (CPE) assay.

Example 6. Compound 1 Exhibits Synergy in Combination with Remdesivir in a SARS CoV-2 CPE Assay Using the assay protocol from Example 5, one or more other additional agents was tested in combination with remdesivir. Each agent was evaluated in a 10-point dose response (high concentration 15 μM→two-fold dilution). The combination treatment exhibited synergy, with a maximum ZIP synergy score of 32.8 and an average plate ZIP synergy score of 5.523 (FIG. 6). Synergy with Compound 1 was realized at concentrations up to ~1 μM whereas concentrations of Compound 1 above 1 μM did not afford synergy due to essentially complete inhibited viral cytopathic effect as a single agent. Remdesivir synergy was realized at concentrations above 0.5 μM.

Figure 7:
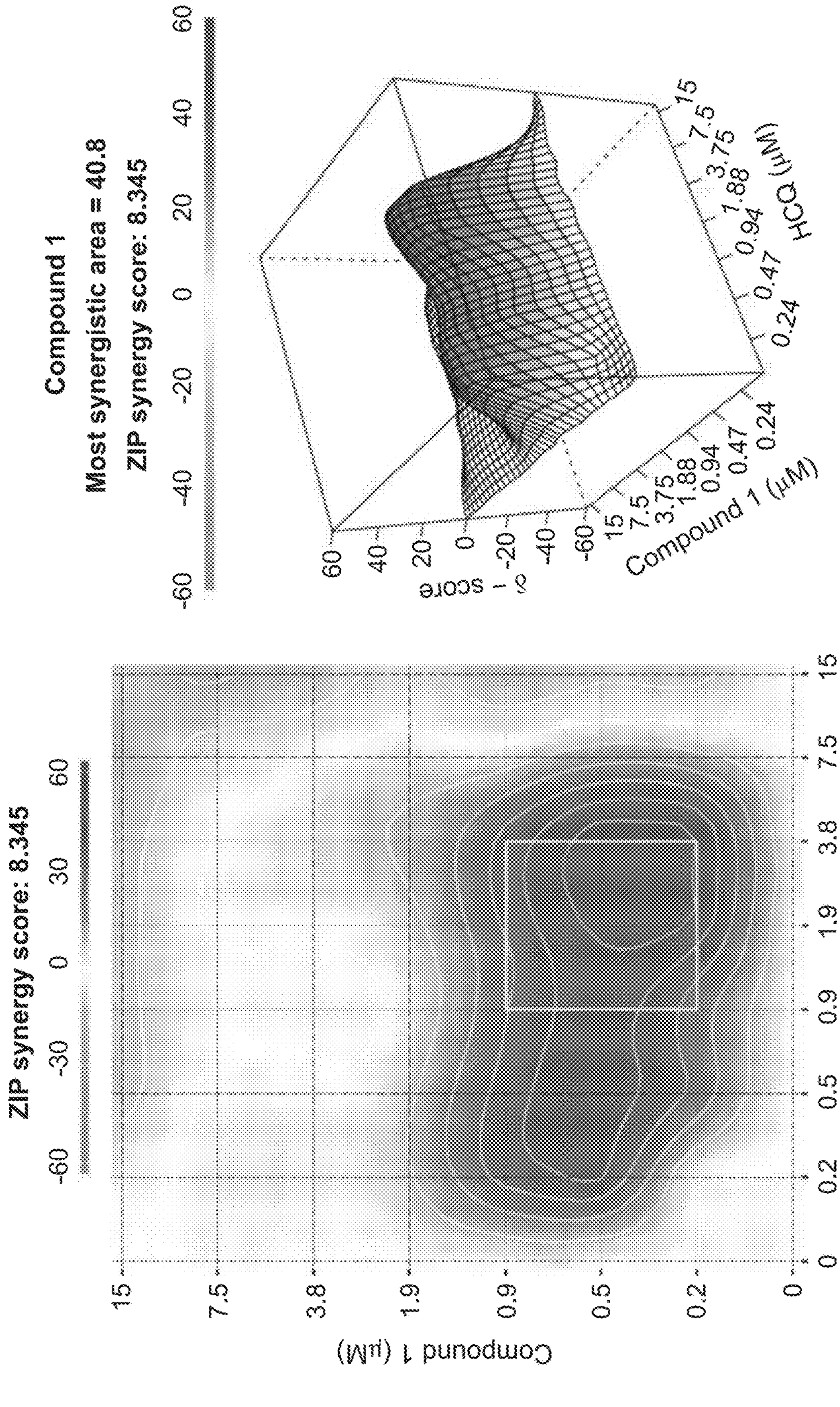
FIG. 7 depicts exemplary synergy analysis of Compound 1 and hydroxychloroquine in a SARS CoV-2 cytopathic effect (CPE) assay.

Example 7. Compound 1 Exhibits Synergy in Combination with Hydroxychloroquine in a SARS CoV-2 CPE Assay Using the assay protocol from Example 5, one or more other additional agents was tested in combination with hydroxychloroquine (HCQ). Each agent was evaluated in a 10-point dose response (high concentration 15 μM→two-fold dilution). The combination treatment exhibited synergy, with a maximum ZIP synergy score of 40.8 and an average plate ZIP synergy score of 8.345 (FIG. 7). Synergy with Compound 1 was realized at concentrations up to ~1.9 μM whereas concentrations of Compound 1 above 1.9 μM did not afford synergy due to essentially complete inhibited viral cytopathic effect as a single agent. HCQ synergy was realized at concentrations between ~0.1 to ~7.5 μM.

Example 8. Compounds 1, 2, 3, 4, and 5 Exhibit Antiviral Activity in a SARS CoV-2 Reporter Assay The Nanoluc reporter virus assay (NLRVA) for SARS-CoV-2 in A549 lung epithelial cells is used to assess anti-SARS CoV-2 activity in a human lung epithelial cell line. Cell viability is measured using Promega Cell Titer Glo. Viral replication is determined by the level of nanoluc luciferase enzyme activity measured by the Promega Nano-Glo® Luciferase Assay System 48 hours post-inoculation of host cells. The assay determines the difference in nanoluc activity between infected and uninfected cells and the variability in the assay is sufficient to yield a Z' factor>0.5. Compound is tested at a top concentration of 2.5 μM with six serial two-fold dilutions down to 0.04 μM as a single agent, or in combination with a second antiviral agent 7-point concentration range (in duplicate) for each compound in the SARS CoV-2 NLRVA using A549 lung epithelial cells expressing ACE2.

Compound 1 was tested in a 7-point dose response (high concentration 2.5 μM→two-fold dilution), affording an $IC_{50}$ of 108 nM for inhibition of SARS CoV-2 mediated cell killing. Compound 1 did not exhibit general cytotoxic effects, affording a CC50>30 M.

Compound 2 was tested in a 7-point dose response (high concentration 2.5 μM→two-fold dilution), affording an $IC_{50}$ of 2,030 nM for inhibition of SARS CoV-2 mediated cell killing. Compound 2 did not exhibit general cytotoxic effects in Vero E6 cells, affording a CC50>30 M.

Compound 3 was tested in a 7-point dose response (high concentration 2.5 μM→two-fold dilution), affording an $IC_{50}$ of >30,000 nM for inhibition of SARS CoV-2 mediated cell killing. Compound 3 did not exhibit general cytotoxic effects in Vero E6 cells, affording a CC50>30 M.

Compound 4 was tested in a 7-point dose response (high concentration 2.5 μM→two-fold dilution), affording an $IC_{50}$ of 520 nM for inhibition of SARS CoV-2 mediated cell killing. Compound 4 did not exhibit general cytotoxic effects in Vero E6 cells, affording a CC50>30 μM.

Compound 5 was tested in a 7-point dose response (high concentration 2.5 μM→two-fold dilution), affording an $IC_{50}$ of 7,734 nM for inhibition of SARS CoV-2 mediated cell killing. Compound 5 did not exhibit general cytotoxic effects in Vero E6 cells, affording a CC50>10 μM.

Example 9. Compound 1 Exhibits Antiviral Activity in a MERS Coronavirus CPE Assay A cell-based assay is used to measure the cytopathic effect (CPE) of the virus infecting Vero E6 host cells. Host cells infected with virus die as a consequence of the virus hijacking the cellular mechanisms for genome replication. The CPE reduction assay indirectly monitors the effect of antiviral agents acting through various molecular mechanisms by measuring the viability of host cells three days after inoculation with virus. Anti-viral compounds are identified as those that protect the host cells from the cytopathic effect of the virus, thereby increasing viability.

Vero E6 cells selected for expression of the SARS CoV receptor (ACE2; angiotensin-converting enzyme 2) are used for the CPE assay. Cells were grown in MEM/10% HI FBS supplemented and harvested in MEM/1% PSG/supplemented 2% HI FBS. Cells are batch inoculated with coronavirus EMC/2012 MERS, at M.O.I.~0.002 which results in 5% cell viability 96 hours post infection. Assay Ready Plates (ARPs; Corning 3712BC) pre-drugged with test compound (30-90 nL sample in 100% DMSO per well dispensed using a Labcyte ECHO 550) are prepared in the BSL-2 lab by adding 5 μL assay media to each well. The plates are passed into the BSL-3 facility where a 25 μL aliquot of virus inoculated cells (4000 Vero E6 cells/well) is added to each well in columns 3-22. The wells in columns 23-24 contain virus infected cells only (no compound treatment). Prior to virus infection, a 25 μL aliquot of cells is added to columns 1-2 of each plate for the cell only (no virus) controls. After incubating plates at 37° C./5% $CO_2$ and 90% humidity for 72 hours, 30 μL of Cell Titer-Glo (Promega) is added to each well. Luminescence is read using a Perkin Elmer Envision or BMG CLARIOstar plate reader following incubation at room temperature for 10 minutes to measure cell viability. Raw data from each test well are normalized to the average signal of non-infected cells (Avg Cells; 100% inhibition) and virus infected cells only (Avg Virus; 0% inhibition) to calculate % inhibition of CPE using the following formula: % inhibition=100*(Test Cmpd−Avg Virus)/(Avg Cells−Avg Virus). The SARS CPE assay is conducted in BSL-3 containment with plates being sealed with a clear cover and surface decontaminated prior to luminescence reading.

Example 10. Compound 1 Exhibits Antiviral Activity in a Hepatitis C (HCV Genotype 1b) Replicon Assay The HCV replicon antiviral evaluation assay examines the effects of compounds at six serial dilutions. An HCV replicon 1b (Con1 strain containing a luciferase reporter) in a Huh7 human hepatoma cell line is used for this assay. Human interferon alpha-2b (rIFNα-2b) is included in each run as a positive control compound. Briefly, the replicon cells are plated at 5,000 cells/well into 96-well plates that are dedicated for the analysis of cell numbers (cytotoxicity) or antiviral activity. On the following day, samples are diluted with assay media and added to the appropriate wells. Cells are processed 72 hours later when the cells are still subconfluent. For the luciferase endpoint assay, HCV replicon levels are assessed as replicon-derived Luc activity. The toxic concentration of drug that reduces cell numbers assessed by the CytoTox-1 cell proliferation assay (Promega) is a fluorometric assay of cell numbers (and cytotoxicity). Where applicable EC50 (concentration inhibiting HCV replicon by 50%), EC90 (concentration inhibiting HCV replicon by 90%), CC50 (concentration decreasing cell viability by 50%), CC90 (concentration decreasing cell viability by 90%) and SI (selectivity indices: CC50/EC50 and CC90/EC90) values are derived.

Example 11. Compound 1 Exhibits Antiviral Activity in a PRVABC59 (Vero Cell) ZIKA CPE Assay The Zika virus cytoprotection assay uses Vero cells and strain PRVABC59. Briefly virus and cells are mixed in the presence of test compound and incubated for 5 days. The virus is pre-titered such that control wells exhibit 85 to 95% loss of cell viability due to virus replication. Therefore, antiviral effect is assessed as a function of cytoprotection. Cytoprotection and compound cytotoxicity are assessed by MTS (CellTiter® 96 Reagent, Promega, Madison Wis.) reduction. The % reduction in viral cytopathic effects (CPE) is determined and reported; EC50 (concentration inhibiting virus-induced cytopathic effects by 50%), CC50 (concentration resulting in 50% cell death) and a calculated SI (selectivity index=CC50/EC50) are provided along with a graphical representation of the antiviral activity and compound cytotoxicity when compounds are tested in dose-response. Each assay includes Interferon-β as a positive control.

Cell Preparation

Vero cells are grown in Dulbecco Minimum Essential Medium (DMEM with Glutamax, Gibco) supplemented with 10% fetal bovine serum (FBS) and sub-cultured twice a week at a split ratio of 1:10 using standard cell culture techniques. Total cell number and percent viability determinations are performed using a hemacytometer and trypan blue exclusion. Cell viability must be greater than 95% for the cells to be utilized in the assay. The cells are seeded in 96-well tissue culture plates the day before the assay at a concentration of 1×104 cells/well. Antiviral assays are performed in DMEM supplemented with glutamine and a reduced concentration FBS of 2%.

Virus Preparation

The virus used for this assay is strain PRVABC59. ZIKV strain PRVABC59 was isolated in 2015 from human serum collected in Puerto Rico and obtained from the Center for Disease Control and Prevention (Division of Vector-borne Infectious Diseases, CDC, Fort Collins, CO and was grown in Vero cells for the production of stock virus pools. For each assay, a pre-titered aliquot of virus is removed from the freezer (−80oC), thawed, re-suspended and diluted into tissue culture medium such that the amount of virus added to each well is the amount determined to provide between 85 to 95% cell killing at 5 days' post-infection.

Compound Dilution Format

Samples are evaluated for antiviral efficacy with triplicate measurements using 6 concentrations at half-log dilutions in order to determine EC50 values and with duplicate measurements to determine cytotoxicity.

Cell Viability

At assay termination (5 days' post-infection), 15 μL of soluble tetrazolium-based MTS (CellTiter® 96 Reagent, Promega) is added to each well. The microtiter plates are then incubated for 1-2 hours at 37° C./5% $CO_2$. MTS is metabolized by the mitochondrial enzymes of metabolically active cells to yield a soluble colored formazan product. Adhesive plate sealers are used in place of the lids and each plate is read via spectrophotometer at 490/650 nm using a Molecular Devices SpectraMax i3 plate reader.

Data Analysis

Using an in-house computer program % Cytopathic Effect (CPE) Reduction, % Cell Viability, EC25, EC50, EC95, CC25, CC50, and CC95 and other indices are calculated.

EQUIVALENTS

While specific embodiments have been discussed, the above specification is illustrative and not restrictive. Many variations of the embodiments will become apparent to those skilled in the art upon review of this specification. The full scope of what is disclosed should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained.

What is claimed is:

1. A method of ameliorating or treating a SARS-CoV-1 or SARS-CoV-2 infection in a patient in need thereof, comprising administering to the patient:

(i) a therapeutically effective amount of a compound represented by:

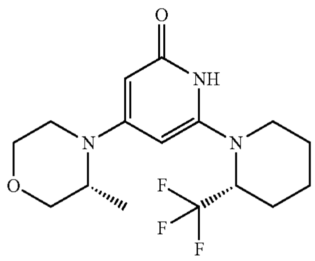

;

and (ii) a therapeutically effective amount of remdesivir or hydroxychloroquine.

* * * * *